(12) United States Patent
Okada

(10) Patent No.: US 12,144,892 B2
(45) Date of Patent: *Nov. 19, 2024

(54) PHARMACEUTICAL COMPOSITION

(71) Applicant: TAIHO PHARMACEUTICAL CO., LTD., Tokyo (JP)

(72) Inventor: Shinji Okada, Tokushima (JP)

(73) Assignee: TAIHO PHARMACEUTICAL CO., LTD., Tokyo (JP)

( * ) Notice: Subject to any disclaimer, the term of this patent is extended or adjusted under 35 U.S.C. 154(b) by 301 days.

This patent is subject to a terminal disclaimer.

(21) Appl. No.: 17/347,989

(22) Filed: Jun. 15, 2021

(65) Prior Publication Data

US 2021/0308056 A1 Oct. 7, 2021

Related U.S. Application Data

(63) Continuation of application No. 16/485,971, filed as application No. PCT/JP2018/005140 on Feb. 14, 2018, now Pat. No. 1,111,062.

(30) Foreign Application Priority Data

Feb. 15, 2017 (JP) .................. 2017-026203

(51) Int. Cl.
    A61K 9/16     (2006.01)
    A61K 31/04    (2006.01)
    A61K 31/47    (2006.01)

(52) U.S. Cl.
    CPC .......... *A61K 9/1652* (2013.01); *A61K 9/1611* (2013.01); *A61K 9/1694* (2013.01); *A61K 31/47* (2013.01); *A61K 31/04* (2013.01)

(58) Field of Classification Search
    CPC .............................. A61K 31/47; A61K 9/1652
    See application file for complete search history.

(56) References Cited

U.S. PATENT DOCUMENTS

| | | | |
|---|---|---|---|
| 5,254,541 A | 10/1993 | Kwong | |
| 7,135,466 B2 | 11/2006 | Sakai et al. | |
| 7,253,286 B2 | 8/2007 | Funahashi et al. | |
| 7,425,564 B2 | 9/2008 | Fujiwara et al. | |
| 7,579,473 B2 | 8/2009 | Bannen et al. | |
| 8,304,427 B2 | 11/2012 | Suda et al. | |
| 9,149,471 B2 | 10/2015 | Miyaura et al. | |
| 10,143,688 B2 | 12/2018 | Sato | |
| 10,449,189 B2 | 10/2019 | Fujioka | |
| 10,695,340 B2 | 6/2020 | Fujioka | |
| 11,110,062 B2 | 9/2021 | Okada | |
| 11,191,759 B2 | 12/2021 | Fujioka | |
| 2004/0053908 A1 | 3/2004 | Funahashi et al. | |
| 2004/0242603 A1 | 12/2004 | Fujiwara et al. | |
| 2004/0246603 A1 | 12/2004 | Rydqvist | |
| 2005/0113284 A1 | 5/2005 | Nakamura et al. | |
| 2006/0160832 A1 | 7/2006 | Funahashi et al. | |
| 2006/0247259 A1 | 11/2006 | Funahashi et al. | |
| 2007/0191369 A1 | 8/2007 | Lauffer et al. | |
| 2008/0161305 A1 | 7/2008 | Forsyth et al. | |
| 2008/0312221 A1 | 12/2008 | Fujiwara et al. | |
| 2009/0118305 A1 | 5/2009 | Barlaam et al. | |
| 2009/0226443 A1 | 9/2009 | Filvaroff et al. | |
| 2009/0274693 A1 | 11/2009 | Gilmer et al. | |
| 2010/0324087 A1 | 2/2010 | Yamamoto | |
| 2010/0063054 A1 | 3/2010 | Bressi et al. | |
| 2010/0190774 A1 | 7/2010 | Lauffer et al. | |
| 2010/0297075 A1 | 11/2010 | Chan et al. | |
| 2011/0034439 A1 | 2/2011 | Suda et al. | |
| 2011/0104161 A1 | 5/2011 | Burgess et al. | |
| 2011/0105747 A1 | 5/2011 | Fujiwara et al. | |
| 2011/0212967 A1 | 9/2011 | Zhuo et al. | |
| 2011/0281865 A1 | 11/2011 | Muthuppalaniappan et al. | |
| 2013/0142790 A1 | 6/2013 | Gilmer et al. | |
| 2013/0150363 A1 | 6/2013 | Gilmer et al. | |
| 2013/0261116 A1 | 10/2013 | Muthuppalaniappan et al. | |
| 2013/0345224 A1 | 12/2013 | Zhuo et al. | |
| 2014/0256804 A1 | 9/2014 | Iwata et al. | |
| 2014/0378409 A1 | 12/2014 | Fujita et al. | |
| 2015/0025082 A1 | 1/2015 | Aven et al. | |
| 2015/0056207 A1 | 2/2015 | Filvaroff et al. | |
| 2015/0133449 A1 | 5/2015 | Muthuppalaniappan et al. | |
| 2015/0164879 A1 | 6/2015 | Miyaura et al. | |
| 2016/0137650 A1 | 5/2016 | Zhuo et al. | |

(Continued)

FOREIGN PATENT DOCUMENTS

| | | |
|---|---|---|
| CN | 1448053 A | 10/2003 |
| CN | 101491240 A | 7/2009 |

(Continued)

OTHER PUBLICATIONS

Office Action issued in corresponding Russian Application 2019125612 dated Jul. 6. 2021, with English Translation.
Stringer J.L. Drug, in: Encyclopedia Britannica//website, URL: https://www.britannica.com/science/drug-chemical-agent.
The Pursuit of Responsible Use of Medicines. Sharing and Learning from Country Experiences. Oct. 2, 2012. Technical document. WHO Reference WHO/EMP/MAR/2012.3. URL: https://www.who.int/publications/i/item/WHO-EMP-MAR-2012.3.
U.S. Appl. No. 14/369,060, filed Jun. 26, 2014, US 2014/037409 A1, Hidenori Fujita, et al.
U.S. Appl. No. 17/347,989, filed Jun. 15, 2021, US 2021/0308056 A1, Shinji Okada.

(Continued)

*Primary Examiner* — Kevin E Weddington
(74) *Attorney, Agent, or Firm* — Oblon, McClelland, Maier & Neustadt, L.L.P.

(57) ABSTRACT

An object of the present invention is to provide a pharmaceutical composition which has excellent stability, disintegratability, and absorbability, is easily prepared, and contains 4-(2-fluoro-4-(3-(2-phenylacetyl)thioureido)phenoxy)-7-methoxy-N-methylquinoline-6-carboxamide or a pharmaceutically acceptable salt thereof and a cyclodextrin derivative. The present invention relates to a pharmaceutical composition containing 4-(2-fluoro-4-(3-(2-phenylacetyl)thioureido)phenoxy)-7-methoxy-N-methylquinoline-6-carboxamide or a pharmaceutically acceptable salt thereof and hydroxypropyl-β-cyclodextrin.

25 Claims, 5 Drawing Sheets

(56) References Cited

U.S. PATENT DOCUMENTS

| | | | |
|---|---|---|---|
| 2017/0088626 A1 | 3/2017 | Jure-Kunkel et al. |
| 2017/0360790 A1 | 12/2017 | Patterson et al. |
| 2018/0092901 A1 | 4/2018 | Denker et al. |
| 2018/0161317 A1 | 6/2018 | Sato |
| 2018/0289690 A1 | 10/2018 | Fujioka |
| 2018/0339054 A1 | 11/2018 | Aven et al. |
| 2019/0263923 A1 | 8/2019 | Jure-Kunkel et al. |
| 2020/0060973 A1 | 2/2020 | Okada |
| 2021/0308056 A1 | 10/2021 | Okada |
| 2022/0040313 A1 | 12/2022 | Aven et al. |

FOREIGN PATENT DOCUMENTS

| | | |
|---|---|---|
| CN | A-101491240 | 7/2009 |
| CN | 101926808 A | 12/2010 |
| CN | A-101926808 | 12/2010 |
| CN | 103889414 A | 6/2014 |
| CN | 105377235 A | 3/2016 |
| CN | A-105377235 | 3/2016 |
| CN | 106551911 A | 4/2017 |
| EP | 1 411 046 A1 | 4/2004 |
| EP | 1 466 624 A1 | 10/2004 |
| EP | 2 287 155 A1 | 2/2011 |
| JP | 5-238958 A | 9/1993 |
| JP | 2003-238592 A | 8/2003 |
| JP | 2005-272474 A | 10/2005 |
| JP | 2008-504366 T | 2/2008 |
| JP | 2009-518296 A | 5/2009 |
| JP | 2011-500778 A | 1/2011 |
| JP | 2012-4860609 B2 | 1/2012 |
| JP | 2013-518887 A | 5/2013 |
| JP | 2013-529207 A | 7/2013 |
| JP | 2016-196411 A | 11/2016 |
| JP | 2017-507155 A | 3/2017 |
| KR | 10-2004-0030690 A | 4/2004 |
| KR | 10-2010-0132023 A | 12/2010 |
| RU | 2013/2494470 C1 | 9/2013 |
| WO | WO 01/47890 A1 | 7/2001 |
| WO | WO 03/000660 A1 | 1/2003 |
| WO | WO 2005/030140 A2 | 4/2005 |
| WO | WO2005-082855 A1 | 9/2005 |
| WO | WO 2005/121125 A1 | 12/2005 |
| WO | WO2006-004636 A2 | 1/2006 |
| WO | WO2006-004833 A2 | 1/2006 |
| WO | WO2006-004884 A2 | 1/2006 |
| WO | WO 2006/104161 A1 | 10/2006 |
| WO | WO 2006/108059 A1 | 10/2006 |
| WO | WO 2007/064797 A2 | 6/2007 |
| WO | WO 2009/053737 A2 | 4/2009 |
| WO | WO 2009/096377 A1 | 8/2009 |
| WO | WO 2009/125597 A1 | 10/2009 |
| WO | WO 2009/137429 A1 | 11/2009 |
| WO | WO 2009/140549 A1 | 11/2009 |
| WO | WO 2010/093789 A2 | 8/2010 |
| WO | WO 2010/150127 A1 | 12/2010 |
| WO | WO-A1-2010-150127 | 12/2010 |
| WO | WO 2011/145035 A1 | 11/2011 |
| WO | WO 2011/162835 A1 | 12/2011 |
| WO | WO 2013/058303 A1 | 4/2013 |
| WO | WO 2013/100014 A1 | 7/2013 |
| WO | WO 2015/046484 A1 | 4/2015 |
| WO | WO 2016/090174 A1 | 6/2016 |
| WO | WO 2016/140717 A1 | 9/2016 |
| WO | WO 2016/175305 A1 | 11/2016 |
| WO | WO2016-208744 A1 | 12/2016 |
| WO | WO2018-151177 A1 | 8/2018 |

OTHER PUBLICATIONS

U.S. Appl. No. 16/645,315, filed Mar. 6, 2020, US 2021-0030738 A1, Tomonori Haruma.
Combined Chinese Office Action and Search Report dated Jan. 25, 2022 in Chinese Patent Application No. 201880012000.X (with unedited computer generated English translation), 18 pages.
Russian Office Actiond dated Feb. 15, 2022 in Russian Patent Application No. 2020109716 (with English translation), 8 pages.
Biochemistry (for food and related specialties), Thrones, pp. 32-33, China Light Industry Press, Jan. 2017 (with English translation).
"Study on inclusion complexation of insoluble drugs with β-cyclodextrin and its derivatives", Series I, Excellent High Paper of China, Full Database Engineering Technology, Mar. 31, 2015, Part I (with partial unedited computer generated English.
M.D.Mashkovskiy. Lekarstvennye sredstva (Medical Agents), 14th edition, vol. 1, Moscow, 2001, p. 11 (partial translation).
Runze Shang, et al., "Cabozantinib-based combination therapy for the treatment of hepatocellular carcinoma," Gut, vol. 70, 2021, pp. 1746-1757.
Runze Shang, et al., "Cabozantinib based combination therapy for the treatment of Hepatocellular Carcinoma," Gut, Supplemental Material, 2020, 52 pages.
"Highlights of Prescribing Information These highlights do not include all the information needed to use CABOMETYX safely and effectively. See full prescribing information for CABOMETYX," Reference ID: 4375294, 32 pages.
Emilien Loeuillard, et al., "Targeting tumor-associated macrophages and granulocytic myeloid-derived suppressor cells augments PD-1 blockade in cholangiocarcinoma," The Journal of Clinical Investigation. vol. 130, No. 10, Oct. 2020, 18 pages.
Supplementary Methods—YAP Signature Differential Expression Analysis, 24 pages.
Hidenori Fujita, et al., "High Potency VEGFRs/MET/FMS Triple Blockade by TAS-115 Concomitantly Suppresses Tumor Progression and Bone Destruction in Tumor-Induced Bone Disease Model with Lung Carcinoma Cells," PLoS One, Oct. 13, 2016, 21 pages.
Shutaro Yamada, et al., "Therapeutic potential of TAS-115 via c-MET and PDGFRα signal inhibition for synovial sarcoma," BMC Cancer, vol. 17, No. 334, 2017, 14 pages.
Hidenori Fujita, et al., "High Potency VEGFRs/MET/FMS Triple Blockade by TAS-115Concomitantly Suppresses Tumor Progression and Bone Destruction in Tumor-Induced Bone Disease Model with Lung Carcinoma Cells," PLoS One, Oct. 13, 2016, 13 pages.
Notification of Reason for Refusal dated Nov. 4, 2021 in Korean Patent Application No. 10-2020-7006381 (with English language translation), 15 pages.
U.S. Appl. No. 14/369,060, filed Jun. 26, 2014, US 2014/0378409 A1, Hidenori Fujita, et al.
"Osteoporosis Prevention, Diagnosis and Therapy", JAMA vol. 285, No. 6, pp. 785-794, Feb. 14, 2001.
T.D. Rachner et al.,"Osteoporosis: now and the future", www.thelancet.com vol. 377, Apr. 9, 2011, pp. 1276-1287.
M. Shiraki et al., Long-Term Treatment of Postmenopausal Osteoporosis with Active Vitamins 03, 1-Alpha-Hydroxycholecalciferol (1α-OHD3) and 1, 24 Dihydroxycholecalciferol (1, 24 (OH)2D2, Endocrinol, Japan 1985, 32 (2) 305-315.
R. Rizzoli et al., "Adverse Reaction and Drug-Drug Interactions in the Management of Woman with Postmenopausal Osteoporosis", Calcif Tissue Int (2011), 89:91-104.
"Risks and Benefits of Estrogen Plus Progestin in Healthy Postmenopausal Women", JAMA. Jul. 17, 2002—vol. 288, No. 3, pp. 321-333.
M.A. Bolognese. "SERMs and SERMs with estrogen for postmenopausal osteoporosis", Rev. Endocr Metab Disord (2010) 11 :253-259.
Lim, V. et al., "New therapeutic targets for osteoporosis: Beyond denosumab", Maturitas 73 (2012), 269-272.
S. Das et al., "Osteoporosis—a current view of pharmacological prevention and treatment", Drug Design. Development and Therapy, 2013:7, pp. 435-448.
E. Canalis, "New Treatment Modalities in Osteoporosis", Endocrine Practice, vol. 16. No. 5, Sep./Oct. 2010, pp. 855-863.
Combined Russian Federation Office Action and Search Report dated Nov. 29, 2019 in Patent Application No. 2017145271 /04(077515) (with English translation).
Notice of Reasons for Refusal dated Jan. 26, 2021 in Japanese Patent Application No. 2017-525457 (with English language translation).

(56) References Cited

OTHER PUBLICATIONS

Extended European Search Report issued in Application No. 18854415.9 dated Apr. 30, 2021.
Zhang Jin et al., "Recent Advances in the development of dual VEGFR and c-Met small molecule inhibitors as anticancer drugs", European Journal of Medicinal Chemistry, Elsevier, Amsterdam, NL, vol. 108, Dec. 13, 2015, pp. 495-504.
Office Action dated Jan. 28, 2021 in corresponding Korean Patent Application No. 10-2019-7023592 (with English Translation), 10 pages.
Kyu Hyun Choi et al., "Hyaluronic acid gel formulation containing Piroxicam: Hydroxypropyl-β-cyclodextrin inclusion complex for intra-articular delivery" (with English abstract), Biomaterials Research 13 (1) :1-6(2009), 6 pages.
George SJ et al., "Studies on the Preparation, Characterization, and Solubility of 2-HP-β-Cyclodextrin-Meclizine HCI Inclusion Complexes", Journal of Young Pharmacists vol. 4 / No. 4, (2012), pp. 220-227.
Korean Office Action dated Nov. 4, 2021 in Korean Patent Application No. 10-2020-7006381 (with English translation), 15 pages.
Combined Russian Office Action and Search Report dated Feb. 15, 2021 in Russian Patent Application No. 2019125612 (with English translation of the Office Action), 15 pages.
Steppeler F. et al.,"Chiral Thioureas-Preparation and Significance in Asymmetric Synthesis and Medicinal Chemistry", Molecules, Jan. 18, 2020, vol. 25, No. 2, Article No. 401, pp. 1 to 56, https://doi.org/10.3390/molecules25020401.
Yamashita, Kazuko et al., "Development. of an On-line Sample Enrichment System Coupled to ESI-TOFMS-Challenge to highly sensitive structural elucidation of impurities of agrochemicals and pharmaceuticals-", Sumitomo Chemical, 2002, vol. II, pp. 56-64 (with English Abstract).
Murakami, Tomonori et al., "Structure Elucidation of Impurities in Pharmaceuticals by HPLC Hyphenated Techniques", Chromatography, 2012, vol. 33, No. 3, pp. 179-190 (with English Abstract).
International Search Report issued in PCT/JP2021/005272 dated Mar. 30, 2021 (with English Translation).
Written Opinion of International Search Report issued in PCT /JP2021/005272 dated Mar. 30, 2021 (with English Translation).
Office Action dated Sep. 30, 2021 in co-pending U.S. Appl. No. 16/645,315, 39 pages.
Lulu Miao, et al., "PD-L1 and c-MET Expression and Survival in Patients with Small Cell Lung Cancer" Oncotarget, vol. 8, No. 33, 2017, pp. 53978-53988.
Patrick A. Ott, et al. "Pembrolizumab in Patients With Extensive-Stage Small-Cell Lung Cancer: Results From the Phase lb Keynote-028 Study", Journal of Clinical Oncology, vol. 35, No. 34, Dec. 1, 2017, pp. 3823-3829 and cover pages.
Office Action issued in corresponding Chinese Appln. 201880012000.X dated Jan. 25, 2022 (with partial English machine Translation).
Biochemistry (No. 2016-2-013) (for food and related specialties), Thrones, pp. 32-33, China Light Industry Press, Jan. 2017—ISBN 978-7-5184-1040-8 (with English Translation).
"Study on inclusion complexation of insoluble drugs with β-cyclodextrin and its derivatives", Series I, Excellent High Paper of China, Full Database Engineering Technology, Part I (with English Translation).
Office Action issued in corresponding Russian Appln 2020109716 dated Feb. 15, 2022 (with English Translation).
M.D.Mashkovskiy. Lekarstvennye sredstva (Medicinal Agents), 14th edition, vol. 1, Moscow, 2001, p. 11 (with partial English translation).
International Search Report dated May 1, 2019 in PCT/JP2018/005140, (with English translation), 5 pages.
Written Opinion of the International Searching Authority dated May 1, 2018 in PCT/JP2018/005140, (with English translation), 11 pages.
International Search Report dated Jun. 28, 2016, in PCT/JP2016/063413, 5 pages.

Office Action dated Mar. 28, 2018 in co-pending U.S. Appl. No. 15/570,021, 6 pages.
Notice of Allowance dated Jul. 26, 2018 in co-pending U.S. Appl. No. 15/570,021, 6 pages.
International Search Report dated May 19, 2009 in PCT/JP2009/01655, 2 pages.
Extended European Search Report dated Apr. 11, 2012 in Patent Application No. 09730440.6, 5 pages.
Notice of Allowance dated Aug. 13, 2012 in co-pending U.S. Appl. No. 12/937,312, 9 pages.
International Search Report dated Feb. 12, 2013 in PCT/JP2012/083794, 3 pages.
Written Opinion of the International Searching Authority dated Feb. 12, 2013 in PCT/JP2012/083794 filed Dec. 27, 2012, 8 pages.
Office Action dated Sep. 24, 2015 in co-pending U.S. Appl. No. 14/369,060, 17 pages.
Extended European Search Report dated Apr. 28, 2015 in Patent Application No. 12863476.3, 8 pages.
Office Action dated Apr. 22, 2016 in co-pending U.S. Appl. No. 14/369,060, 25 pages.
Office Action dated Apr. 21, 2017 in co-pending U.S. Appl. No. 14/369,060, 29 pages.
Office Action dated Nov. 30, 2017 in co-pending U.S. Appl. No. 14/369,060, 17 pages.
Office Action dated Aug. 21, 2019 in co-pending U.S. Appl. No. 14/369,060, 19 pages.
International Search Report dated Sep. 13, 2016 in PCT/JP2016/068902, 3 pages.
Office Action dated Sep. 20, 2018 in co-pending U.S. Appl. No. 15/574,060, 8 pages.
Extended European Search Report dated Jan. 30, 2019 in Patent Application No. 16814513.4, 8 pages.
Notice of Allowance dated Jun. 17, 2019 in co-pending U.S. Appl. No. 15/574,060, 8 pages.
Hidenori Fujita, et al., "The Novel VEGF Receptor/MET-Targeted Kinase Inhibitor TAS-115 Has Marked In Vivo Antitumor Properties and a Favorable Tolerability Profile" Molecular Cancer Therapeutics, vol. 12, No. 12, Dec. 2013, pp. 2685-2696 and cover page.
"Poster Session—Met, Ret and Notch", European Journal of Cancer, vol. 48, No. 6, Nov. 8, 2012, p. 94.
Masako Yokoo, et al., "2-Hydroxypropyl-β-Cyclodextrin Acts as a Novel Anticancer Agent", PLOS One, vol. 10, No. 11, Nov. 4, 2015, pp. 1-20.
Chisa Imamura, "Applied Technology of Cyclodextrin Popular Edition", CMC Publishing Co., Ltd., 2013, pp. 253-261 (with partial English translation).
Kazuhide Ashizawa, et al. "Polymorphic Phenomena of Drug and Science of Crystallization Development and Production and Trend of Regulation", Iyakuhin no Takei Gensho to Shoseki no Kagaku, 2002, 77 pages. (with English translation).
Mino R. Caira, "Crystalline Polymorphism of Organic Compounds", Topics in Current Chemistry, vol. 198, 1998, pp. 163-208.
Bradley D. Anderson, et al., "Preparation of Water-Soluble Organic Compounds Through Salt Formation", (Edited by Wermuth, C.G), Saishin Soyaku Kagaku Last Volume, 1999, 65 pages (with English translation).
Stephen M. Berge et al., "Pharmaceutical Salts", Journal of Pharmaceutical Sciences, vol. 66, No. 1, Jan. 1977, pp. 1-19.
James G. Christensen, et al., "c-Met as a Target for Human Cancer and Characterization of Inhibitors for Therapeutic Intervention", Cancer Letters, vol. 225, 2005, pp. 1-26.
K. Michael Weidner, et al., "Scatter Factor: Molecular Characteristics and Effect on the Invasiveness of Epithelial Cells", the Journal of Cell Biology, vol. 111, Nov. 1990, pp. 2097-2108.
Paolo M. Comoglio, et al., "Scatter Factors and Invasive Growth", Cancer Biology, vol. 11, 2001, pp. 153-165.
Xiaohua Xin, et al., "Hepatocyte Growth Factor Enhances Vascular Endothelial Growth Factor-Induced Angiogenesis in Vitro and in Vivo", American Journal Of Pathology, vol. 158, No. 3, Mar. 2001, pp. 1111-1120.

(56) References Cited

OTHER PUBLICATIONS

Eiji Ichimura, et al., "Expression of c-*met*/HGF Receptor in Human Non-small Cell Lung Carcinomas in vitro and in vivo and its Prognostic Significance", JPN J. Cancer Res, vol. 87, Oct. 1996, pp. 1063-1069.

Masakazu Nakajima, et al., "The Prognostic Significance of Amplification and Overexpression of c-*met* and c-*erb* B-2 in Human Gastric Carcinomas", Cancer, vol. 85, No. 9, May 1, 1999, pp. 1894-1902.

Wilfredo Hernandez, et al., "Synthesis, Characterization and Antitumor Activity of Copper (II) Complexes, [CuL$_2$] [HL $^{1-3}$=N,N-Diethyl-N'-(R-Benzoyl) Thiourea (R=H, o—Cl and p—NO$_2$)]", Bioinorganic Chemistry and Applications, vol. 3, Nos. 3-4, 2005, pp. 299-316.

Xiao-Ping Rao, et al., "Synthesis and Antitumor Activities of Unsymmetrically Disubstituted Acylthioureas Fused with Hydrophenanthrene Structure", Medicinal Chemistry Research, vol. 20, 2011, pp. 333-338.

Takahumi Nishii, et al., "c-Met Inhibitors Intensify the Sensitivity to Anticancer Agents of Gastric Cancer Stem Cell-Like SP Cells", Journal of Japan Society for Cancer Therapy, vol. 43, No. 2, 2008, p. 390, (with Partial English translation).

Takehito Shukuya, et al. "Paradigm Shift from Non-Selective Treatment to Selective Treatment", Mebio Oncology, vol. 6, No. 1, 2009, pp. 23-31, (with Partial English translation).

Takashi Seto. "Trend of Molecular Target Therapy—from ASCO 2010 ASCO Report: Lung Cancer", Cancer Molecular Target Therapy, vol. 8, No. 4, 2010, pp. 267-270, (with Partial English translation).

Toshimitsu Uenaka, et al., "2. Current Status of Development of Molecular Therapeutic Drugs Targeting HGF/c-Met", Experimental Medicine, vol. 29, No. 2, 2011, pp. 303-309, (with Partial English translation).

Seiji Yano, et al., "Resistance to EGFR-TK Inhibitors Induced by HGF/MET Signaling", Respiratory Medicine, vol. 17, No. 3, 2010, pp. 283-288, (with Partial English translation).

K. M. Weidner, et al., "Scatter Factor: Molecular Characteristics and Effect on the Invasiveness of Epithelial Cells", The Journal of Cell Biology, vol. 111, Nov. 1990, pp. 2097-2108.

Takafumi Nishii, et al., "c-Met Inhibitor Might be a Promising Molecular-Targeted Molecule Against for CPT11-Resistant Cancer Stem Cells", AACR Annual Meeting, XP 055182601, 2009, 2 pages.

Sheng-Hua Chu, et al., "c-Met Antisense Oligodeoxynucleotides Increase Sensitivity of Human Glioma Cells to Paclitaxel", Oncology Reports, vol. 24, No. 1, XP 009183704, Jul. 1, 2010, pp. 189-194.

Isaiah J. Fidler, "Tumor Heterogeneity and the Biology of Cancer Invasion and Metastasis" Cancer Research, vol. 38, Sep. 1978, pp. 2651-2660.

"Benign Tumors" Healthline Website, www.healthline.com/health/benign#overview1, Accessed Mar. 29, 2017, 6 pages.

Stephen Neidle, "Cancer Drug Design and Discovery" Elsevier/Academic Press, 2008, pp. 427-431.

P. Spagnolo, et al., "Idiopathic Pulmonary Fibrosis: Recent Advances on Pharmacological Therapy" Pharmacology & Therapeutics, 2015, 10 Pages.

Richard Hubbard, et al., "Lung Cancer and Cryptogenic Fibrosing Alveolitis, A Population-Based Cohort Study" American Journal of Respiratory and Critical Care Medicine, vol. 161, 2000, pp. 5-8.

David M. Spain, "The Association of Terminal Bronchiolar Carcinoma with Chronic Interstitial Inflammation and Fibrosis of the Lungs" Am Rev Tuberc, 1957, pp. 559-567.

Arnab Datta, et al., "Novel Therapeutic Approaches for Pulmonary Fibrosis" British Journal of Pharmacology, vol. 163, 2011, pp. 141-172.

Lu Zhao, et al. "Paracrine Activation of MET Promotes Peritoneal Carcinomatosis in Scirrhous Gastric Cancer" Cancer Science, vol. 104, No. 12, XP002787868, Dec. 2013, pp. 1640-1646.

International Search Report and Written Opinion dated Dec. 4, 2018, in PCT/JP2018/033108, 36 pages (with English translation).

PLoS One, "High Potency VEGFRs/MET/FMS Triple Blockade by TAS-115 Concomitantly Suppresses Tumor Progression and Bone Destruction in Tumor-Induced Bone Disease Model with Lung Carcinoma Cells", 11 (10): e0164830 (2016), 21 pages.

Cancer Cell, "Targeting Tumor-Associated Macrophages with Anti-CSF-1R Antibody Reveals a Strategy for Cancer Therapy" 25: 846-859 (2014), 14 pages.

Frontiers in Immunology, "Functional relationship between tumor-associated macrophages and macrophage colony-stimulating factor as contributors to cancer progression", 5: Article 489 (2014). 15 pages.

Cancers. "The Role of TAM Family Receptors in Immune Cell Function: Implications for Cancer Therapy". 8 (10), 97: 8100097 (2016), 22 pages.

Cancers. "The Receptor Tyrosine Kinase AXL in Cancer Progression", 8 (11), 103: 8110103 (2016), 16 pages.

Nat. Rev. Cancer, "The blockade of immune checkpoints in cancer immunotherapy", 12 (4): 252-264 (2012), 31 pages.

The New England Journal of Medicine, "Safety, Activity, and Immune Correlate of Anti-PD-1 Antibody in Cancer", 366: 26: 2443-2454 (2012), 12 pages.

Cell, "Primary, Adaptive, and Acquired Resistance to Cancer Immunotherapy", 168 (4): 707-723 (2017), 17 pages.

Science Translational Medicine, "In vivo imaging reveals a tumor-associated macrophage-mediated resistance pathway in anti-PD-1 therapy", 9 (389): eaal 3604 (2017), 11 pages.

International Search Report dated May 1, 2018 in PCT/JP2018/005140, (with English translation), 5 pages.

Amin, A. et al., "Nivolumab (anti-PD-1 : BMS-936558, ON0-4538) in combination with sunitinib or pazopanib in patients (pts) with metastatic renal cell carcinoma (mRCC)", Journal of Clinical Oncology, Jan. 2017, vol. 32, No. 15 supply (May 2014), 3 pages.

Fujita, H, et al, "The Novel VEGF Receptor/MET-Targeted Kinase Inhibitor TAS-115 Has Marked In Vivo Antitumor Properties and a Favorable Tolerability Profile", Molecular Cancer Therapeutics, 2013, vol. 12, No. 12, pp. 2685-2696.

Manegold, C. et al., "The Potential of Combined Immunotherapy and Antiangiogenesis for the Synergistic Treatment of Advanced NSCLC", Journal of Thoracic Oncology, Feb. 2017, vol. 12, No. 2, pp. 194-207.

Lee, C-H. et al., "A phase 1b/2 trial of lenvatinib plus pembrolizumab in patients with renal cell carcinoma.", Annals of Oncology, Aug. 31, 2017, vol. 28, Supply. 5, pp. v295-v296.

Kato Yu, "Combination mechanism of Lenvatinib with immune checkpoint inhibitor by cancer immunity regulation", Japanese Society of Hepato-Biliary-Pancreatic Surgery, Aug. 2017, vol. 75, No. 2, pp. 473-477 (with English abstract).

Kato, Y. et al., "Lenvatinib mesilate (LEN) enhanced antitumor activity of a PD-1 blockade agent by potentiating Th1 immune response.", Annals of Oncology, 2016, vol. 27, Supply. 6, Abstract No. 2PD., ISSN 1569-8041.

Nadal, R. et al., "Final results of a . . . in patients (pts) with metastatic urothelial carcirma (mUC) and other genitourinary (GU) malignancies.", Annals of Oncology, Aug. 31, 2017, vol. 28, supply 5, p. v295.

Davare, M. A. et al., "Structural Insight into selectivity and resistance profiles of ROS1 tyrosine kinase inhibitors", PNAS, 2015, vol. 112, No. 39, pp. E5381-E5390.

Bentzien, F. et al., "In Vitro and In Vivo Activity of Cabozantinib (XL184), an Inhibitor of RET, MET, and VEGFR2, in a Model of Medullary Thyroid Cancer", Thyroid, 2013, vol. 23, No. 12, pp. 1569-1577.

Office Action issued in corresponding Russian Application No. 2019125612 dated Feb. 15, 2021 (with English Translation).

Handbook of Pharmaceutical Excipients. 6th ed. Eds: Rowe R.C. et al. Pharmaceutical Press and American Pharmacists Association 2009. 888 pages.

Arun R. et al. Cyclodextrins as Drug Carrier Molecule: A Review // Sci Pharm. 2008. vol. 76. p. 567-598 URL: https://www.mdpi.com/2218-0532/76/4/567.

Jantarat C. et al. Curcumin-Hydroxypropyl-β-Cyclodextrin Inclusion Complex Preparation Methods: Effect of Common Solvent

(56) References Cited

OTHER PUBLICATIONS

Evaporation, Freeze Drying, and pH Shift on Solubility and Stability of Curcumin // Trop J Pharm Res. 2014. vol. 13(8). p. 1215-1223.

Alonso E.C.P. et al. Development of carvedilol-cyclodextrin inclusion complexes using fluid-bed granulation: a novel solid-state complexation alternative with technological advantages // J Pharm Pharmacol. 2016. vol. 68(10). p. 1299-1309.

Mark R. Litzow, et al "A randomized trial of three novel regimens for recurrent acute myeloid leukemia demonstrates the continuing challenge of treating this difficult disease", Wiley - Research Article, 1 page.

John F. Seymour, et al., "Venetoclax-Rituximab in Relapsed or Refractory Chronic Lymphocytic Leukemia", The New England Journal of Medicine, Mar. 22, 2018, 2 pages.

Courtney D. DiNardo, et al., "Venetoclax combined with decitabine or azacitidine in treatment-naive, elderly patients with acute myeloid leukemia", Blood - Plenary Paper - Clinical Trials and Observations, 3Jan.2018, vol. 122, No. 1, 11 pages.

Pin Wu, et al., PD-L 1 and Survival in Solid Tumors: A Meta-Analysis; PLOS One I DOI:10.1371/journal.pone.0131403 Jun. 26, 2015, 15 Pages.

Ze-Jun Zhou, et al., PD-L 1 over-expression and survival in patients with non-small cell lung cancer: a meta-analysis, Transl Lung Cancer Res 2015;4(2):203-208, 6 pages.

Yaqi Li, et al., Prognostic impact of programed cell death-1 (PD-1) and PD-ligand 1 (PD-L 1) expression in cancer cells and tumor infiltrating lymphocytes in colorectal cancer, Molecular Cancer, (2016) 15:55, 15 pages.

Jian Guan, MD, PhD, et al., Programmed Death Ligand-1 (PD-L 1) Expression in the Programmed Death Receptor-1 (PD-1)/PD-L 1 Blockade, Review Article, Arch Pathol Lab Med-vol. 141, Jun. 2017, 11 pages.

Noah Frydenlund BS, MS, et al., PD-L 1 and immune escape: insights from melanoma and other lineage-unrelated malignancies, Elsevier, Human Pathology, Jun. 2017; 21 pages.

Ke Ma, et al., PD-L 1 and PD-1 expression correlate with prognosis in extrahepatic cholangiocarcinoma, Oncology Letters 14: 250-256, 2017, 7 pages.

Overman, et al., "Nivolumab in patients with metastatic DNA mismatch repair-deficient or microsatellite instability-high colorectal cancer (CheckMate 142): an open-label, multicentre, phase 2 study", Lancet Oncology 2017 18:1182 (Year: 2017), 10 pages.

Office Action issued on Sep. 18, 2024 in the related European Patent Application No. 18854415.9.

PHARMACEUTICAL COMPOSITION

This application claims priority to application Ser. No. 16/485,971, filed Aug. 14, 2019, pending, the entire contents of which is incorporated by reference, which application is a national stage application of PCT/JP2018/005140, filed Feb. 14, 2018, which claims benefit of Japanese application 2017-026203 filed Feb. 15, 2017, the entire contents of both applications are incorporated herein by reference.

TECHNICAL FIELD

The present invention relates to a pharmaceutical composition containing 4-(2-fluoro-4-(3-(2-phenylacetyl)thioureido)phenoxy)-7-methoxy-N-methylquinoline-6-carboxamide or a pharmaceutically acceptable salt thereof and hydroxypropyl-β-cyclodextrin, particularly a pharmaceutical composition for oral administration.

BACKGROUND ART

Cyclodextrins and derivatives thereof are widely generally known as an excipient for s improving the solubility of a hydrophobic compound in water. However, most of them are liquid formulations in which the whole or a part of a hydrophobic compound is included inside a cyclodextrin. Therefore, a solid formulation in which a cyclodextrin or a derivative thereof is physically added to improve the solubility is not well known.

At present, as a compound having excellent c-Met/VEGFR2 inhibitory activity and showing antitumor activity, 4-(2-fluoro-4-(3-(2-phenylacetyl)thioureido)phenoxy)-7-methoxy-N-methylquinoline-6-carboxamide (hereinafter, also referred to as "compound 1") has been reported (PTL 1 and 2, and NPL 1 and 2). It has also been reported that the compound 1 is useful as a therapeutic agent for osteoporosis (PTL 3). Further, mesylates of the compound 1 and crystals thereof have also been reported (PTL 4).

However, these reports contain no mention of a pharmaceutical composition containing the compound 1 or a pharmaceutically acceptable salt thereof and a cyclodextrin or a derivative thereof.

CITATION LIST

Patent Literature

PTL 1: WO 2009/125597
PTL 2: WO 2013/100014
PTL 3: WO 2015/046484
PTL 4: WO 2016/175305

Non Patent Literature

NPL 1: Molecular Cancer Therapeutics; 12(12); pp. 2685-96, 2013
NPL 2: European Journal of Cancer; 48(6); p. 94; 2012

Summary of Invention

Technical Problem

The present invention provides a pharmaceutical composition which has excellent stability, disintegratability, and absorbability, is easily prepared, and contains the compound 1 or a pharmaceutically acceptable salt thereof.

Solution to Problem

In view of this, the present inventor found that by adding hydroxypropyl-β-cyclodextrin (HP-β-CD) to the compound 1 or a pharmaceutically acceptable salt thereof, a pharmaceutical composition which has excellent stability, has excellent stability, disintegratability, and absorbability, and is easily prepared can be obtained, and thus completed the present invention.

That is, the present invention relates to the following [1] to [35].

[1] A pharmaceutical composition, containing 4-(2-fluoro-4-(3-(2-phenylacetyl)thioureido)phenoxy)-7-methoxy-N-methylquinoline-6-carboxamide or a pharmaceutically acceptable salt thereof and hydroxypropyl-β-cyclodextrin.

[2] The pharmaceutical composition according to [1], wherein the composition 30 includes peaks at at least 5 or more diffraction angles 2θ (±0.2°) selected from 6.5, 7.8, 9.6, 12.4, 18.8, 21.2, 23.0, 24.5, and 26.0 (°) in powder X-ray structure diffraction.

[3] The pharmaceutical composition according to [1] or [2], wherein the composition includes peaks at diffraction angles 2θ (±0.2°) of 6.5, 7.8, 9.6, 12.4, 18.8, 21.2, 23.0, 24.5, and 26.0 (°) in powder X-ray structure diffraction.

[4] The pharmaceutical composition according to any one of [1] to [3], wherein the composition includes peaks at chemical shift values [δ (ppm)] of 162.6, 130.4, 103.1, 82.7, 73.3, 41.9, and 19.9 in solid $^{13}$C-NMR.

[5] The pharmaceutical composition according to any one of [1] to [4], wherein the composition includes peaks at at least 5 or more absorption bands selected from 1663, 1352, 1225, 1156, 1032, 720, and 553 (cm$^{-1}$) in an infrared absorption spectrum.

[6] The pharmaceutical composition according to any one of [1] to [5], wherein hydroxypropyl-β-cyclodextrin is contained at 0.1 to 5.5 parts by mass with respect to 1 part by mass of 4-(2-fluoro-4-(3-(2-phenylacetyl)thioureido)phenoxy)-7-methoxy-N-methylquinoline-6-carboxamide or a pharmaceutically acceptable salt thereof.

[7] The pharmaceutical composition according to any one of [1] to [6], further containing a silicic acid derivative.

[8] The pharmaceutical composition according to any one of [1] to [7], further containing a cellulose derivative.

[9] The pharmaceutical composition according to any one of [1] to [8], wherein the pharmaceutical composition is a tablet or a granule.

[10] The pharmaceutical composition according to any one of [1] to [9], wherein the pharmaceutical composition is for oral administration.

[11] The pharmaceutical composition according to any one of [1] to [10], wherein the pharmaceutical composition is a tablet.

[12] The pharmaceutical composition according to any one of [1] to [10], wherein the pharmaceutical composition is a tablet having a maximum diameter of 5 mm or less.

[13] A pharmaceutical composition, containing 4-(2-fluoro-4-(3-(2-phenylacetyl)thioureido)phenoxy)-7-methoxy-N-methylquinoline-6-carboxamide or a pharmaceutically acceptable salt thereof and hydroxypropyl-β-cyclodextrin, the pharmaceutical composition produced by physical mixing.

[14] The pharmaceutical composition according to [13], wherein the physical mixing is a production method that does not include a step in which 4-(2-fluoro-4-(3-(2-phenylacetyl)thioureido)phenoxy)-7-methoxy-N-methylquinoline-6-carboxamide or a pharmaceutically acceptable salt thereof is converted into a solution state when the pharmaceutical composition is produced.

[15] The pharmaceutical composition according to [13] or [14], wherein the physical mixing is mixing or granulation.
[16] The pharmaceutical composition according to any one of [13] to [15], wherein the physical mixing is mixing, a dry granulation method, or a wet granulation method.
[17] The pharmaceutical composition according to any one of [13] to [16], wherein the physical mixing is mixing, a crushing granulation method, a fluidized bed granulation method, a rolling bed granulation method, an extrusion granulation method, or a high shear granulation method.
[18] The pharmaceutical composition according to any one of [13] to [17], wherein the physical mixing is a fluidized bed granulation method.
[19] The pharmaceutical composition according to any one of [13] to [18], wherein the composition includes peaks at at least 5 or more diffraction angles 2θ (±0.2°) selected from 6.5, 7.8, 9.6, 12.4, 18.8, 21.2, 23.0, 24.5, and 26.0 (°) in powder X-ray structure diffraction.
[20] The pharmaceutical composition according to any one of [13] to [19], wherein the composition includes peaks at diffraction angles 2θ (±0.2°) of 6.5, 7.8, 9.6, 12.4, 18.8, 21.2, 23.0, 24.5, and 26.0 (°) in powder X-ray structure diffraction.
[21] The pharmaceutical composition according to any one of [13] to [20], wherein the composition includes peaks at chemical shift values [δ (ppm)] of 162.6, 130.4, 103.1, 82.7, 73.3, 41.9, and 19.9 in solid $^{13}$C-NMR.
[22] The pharmaceutical composition according to any one of [13] to [21], wherein the composition includes peaks at at least 5 or more absorption bands selected from 1663, 1352, 1225, 1156, 1032, 720, and 553 ($cm^{-1}$) in an infrared absorption spectrum.
[23] The pharmaceutical composition according to any one of [13] to [22], wherein hydroxypropyl-β-cyclodextrin is contained at 0.1 to 5.5 parts by mass with respect to 1 part by mass of 4-(2-fluoro-4-(3-(2-phenylacetyl)thioureido)phenoxy)-7-methoxy-N-methylquinoline-6-carboxamide or a pharmaceutically acceptable salt thereof.
[24] The pharmaceutical composition according to any one of [13] to [23], further containing a silicic acid derivative.
[25] The pharmaceutical composition according to any one of [13] to [24], further containing a cellulose derivative.
[26] The pharmaceutical composition according to any one of [13] to [25], wherein the pharmaceutical composition is a granule.
[27] The pharmaceutical composition according to any one of [13] to [26], wherein the pharmaceutical composition is for oral administration.
[28] The pharmaceutical composition according to any one of [13] to [27], wherein the pharmaceutical composition is a tablet.
[29] The pharmaceutical composition according to any one of [13] to [28], wherein the pharmaceutical composition is a tablet having a maximum diameter of 5 mm or less.

[30] A method for producing a pharmaceutical composition, obtainable by performing physical mixing of 4-(2-fluoro-4-(3-(2-phenylacetyl)thioureido)phenoxy)-7-methoxy-N-methylquinoline-6-carboxamide or a pharmaceutically acceptable salt thereof and hydroxypropyl-β-cyclodextrin.
[31] The production method according to [30], wherein the physical mixing is a production method that does not include a step in which 4-(2-fluoro-4-(3-(2-phenylacetyl)thioureido)phenoxy)-7-methoxy-N-methylquinoline-6-carboxamide or a pharmaceutically acceptable salt thereof is converted into a solution state when the pharmaceutical composition is produced.
[32] The production method according to [30] or [31], wherein the physical mixing is mixing or granulation.
[33] The production method according to any one of [30] to [32], wherein the physical mixing is mixing, a dry granulation method, or a wet granulation method.
[34] The production method according to any one of [30] to [33], wherein the physical mixing is mixing, a crushing granulation method, a fluidized bed granulation method, a rolling bed granulation method, an extrusion granulation method, or a high shear granulation method.
[35] The production method according to any one of [30] to [34], wherein the physical mixing is a fluidized bed granulation method.

The present invention also relates to the following aspects.

A pharmaceutical composition for preventing and/or treating a tumor, containing 4-(2-fluoro-4-(3-(2-phenylacetyl)thioureido)phenoxy)-7-methoxy-N-methylquinoline-6-carboxamide or a pharmaceutically acceptable salt thereof and hydroxypropyl-β-cyclodextrin.

An antitumor agent, containing 4-(2-fluoro-4-(3-(2-phenylacetyl)thioureido)phenoxy)-7-methoxy-N-methylquinoline-6-carboxamide or a pharmaceutically acceptable salt thereof and hydroxypropyl-β-cyclodextrin.

Use of 4-(2-fluoro-4-(3-(2-phenylacetyl)thioureido)phenoxy)-7-methoxy-N-methylquinoline-6-carboxamide or a pharmaceutically acceptable salt thereof and hydroxypropyl-β-cyclodextrin for producing an antitumor agent.

A method for preventing and/or treating a tumor, including a step of administering a pharmaceutical composition containing 4-(2-fluoro-4-(3-(2-phenylacetyl)thioureido)phenoxy)-7-methoxy-N-methylquinoline-6-carboxamide or a pharmaceutically acceptable salt thereof and hydroxypropyl-β-cyclodextrin to a subject in an effective amount for the treatment and/or prevention.

Use of a pharmaceutical composition containing 4-(2-fluoro-4-(3-(2-phenylacetyl)thioureido)phenoxy)-7-methoxy-N-methylquinoline-6-carboxamide or a pharmaceutically acceptable salt thereof and hydroxypropyl-β-cyclodextrin for preventing and/or treating a tumor.

A pharmaceutical composition for inhibiting c-Met and/or VEGFR2, containing 4-(2-fluoro-4-(3-(2-phenylacetyl)thioureido)phenoxy)-7-methoxy-N-methylquinoline-6-carboxamide or a pharmaceutically acceptable salt thereof and hydroxypropyl-G-cyclodextrin.

An inhibitor for c-Met and/or VEGFR2, containing 4-(2-fluoro-4-(3-(2-phenylacetyl)thioureido)phenoxy)-7-methoxy-N-methylquinoline-6-carboxamide or a pharmaceutically acceptable salt thereof and hydroxypropyl-β-cyclodextrin.

Use of 4-(2-fluoro-4-(3-(2-phenylacetyl)thioureido) phenoxy)-7-methoxy-N-methylquinoline-6-carboxamide or a pharmaceutically acceptable salt thereof and hydroxypropyl-β-cyclodextrin for producing an inhibitor for c-Met and/or VEGFR2.

Use of a pharmaceutical composition containing 4-(2-fluoro-4-(3-(2-phenylacetyl)thioureido)phenoxy)-7-methoxy-N-methylquinoline-6-carboxamide or a pharmaceutically acceptable salt thereof and hydroxypropyl-β-cyclodextrin for inhibiting c-Met and/or VEGFR2.

In these aspects, the above-mentioned features of the invention of this application can be included.

Advantageous Effects of Invention

According to the present invention, a pharmaceutical composition which has excellent stability, disintegratability, and absorbability, is easily prepared, and contains the compound 1 or a pharmaceutically acceptable salt thereof and a cyclodextrin derivative can be provided.

DESCRIPTION OF EMBODIMENTS

Figure 1:
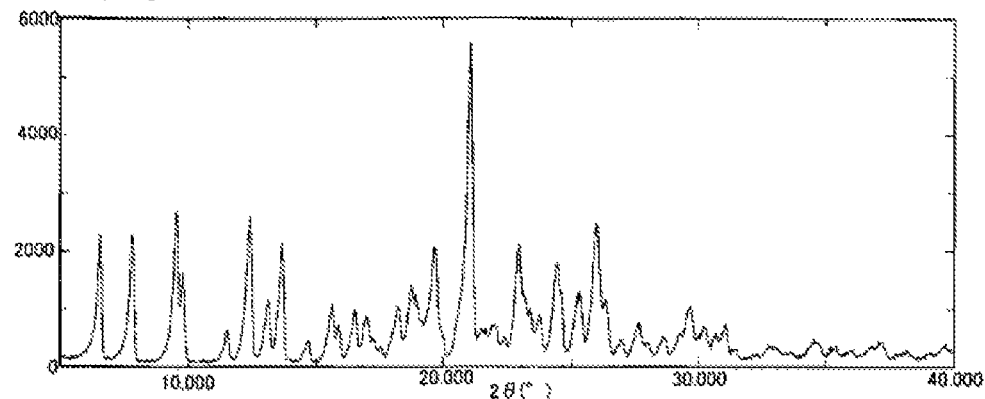
FIG. 1 shows the results of powder X-ray diffraction spectrum (XRD) measurement of a mesylate salt of the compound 1.

An active ingredient of the pharmaceutical composition of the present invention is the compound 1. The compound 1 is 4-(2-fluoro-4-(3-(2-phenylacetyl)thioureido)phenoxy)-7-methoxy-N-methylquinoline-6-carboxamide and the structure thereof is shown below.

[Chem. 1]

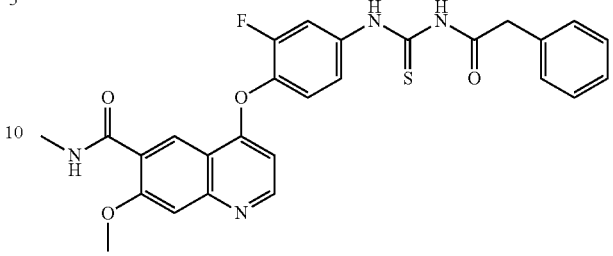

(compound 1)

As the pharmaceutically acceptable salt of the compound 1 to be used in the present invention, salts such as acid addition salts are exemplified, and preferred is a mesylate salt, and more preferred is mono mesylate.

The compound 1 or a pharmaceutically acceptable salt thereof may be a solvate (for example, a hydrate or the like) or a non-solvate, and in the present invention, both are included in "the compound 1 or a pharmaceutically acceptable salt thereof". The compound 1 or a pharmaceutically acceptable salt thereof can be produced by a method described in, for example, PTL 1 or 4.

The compound 1 or a pharmaceutically acceptable salt thereof to be used in the present invention is contained in an amount of preferably 67 mass % or less, more preferably from 5 to 40 mass %, further more preferably from 10 to 20 mass % with respect to the total pharmaceutical composition.

In the cyclodextrin derivative, not only α-cyclodextrin (α-CD), β-cyclodextrin (β-CD), and γ-cyclodextrin (γ-CD), but also hydroxypropyl-β-cyclodextrin (HP-β-CD), sulfobutylether-β-cyclodextrin (SBE-β-CD), and the like are included. However, from the viewpoint of dissolubility, stability, absorbability, etc., the cyclodextrin derivative of the present invention is hydroxypropyl-β-cyclodextrin. The amount of hydroxypropyl-β-cyclodextrin to be used in the present invention may be any as long as the absorbability of the compound 1 or a pharmaceutically acceptable salt thereof to be used in the present invention is improved, and the toxicity of hydroxypropyl-β-cyclodextrin is not appeared.

The amount of hydroxypropyl-β-cyclodextrin to be used in the present invention is preferably 30 mass % or more, more preferably from 60 to 95 mass %, further more preferably from 76 to 85 mass % with respect to the total pharmaceutical composition.

The amount of hydroxypropyl-β-cyclodextrin to be used in the present invention is preferably from 0.1 to 5.5 parts by mass, more preferably from 4.0 to 5.0 parts by mass with respect to 1 part by mass of the compound 1 or a pharmaceutically acceptable salt thereof.

As the pharmaceutical composition of the present invention, a composition in which the compound 1 or a pharmaceutically acceptable salt thereof and hydroxypropyl-Q-cyclodextrin do not form a clathrate or partially form a clathrate is exemplified. That is, it can be confirmed by a powder X-ray diffraction spectrum, solid NMR, IR, etc. that in the pharmaceutical composition of the present invention, one in which the compound 1 or a pharmaceutically acceptable salt thereof and hydroxypropyl-β-cyclodextrin do not form a clathrate is present.

In addition, an error of a peak at a diffraction angle 2θ in a powder X-ray diffraction spectrum in the present invention is about ±0.2°. This is an error caused by an apparatus used in measurement, preparation of a sample, a data analysis method, or the like. Therefore, when a crystal is subjected to XRD measurement in the present invention, an error of ±0.2° of the obtained diffraction angle 2θ is taken into consideration. Further, for the same reason, in the present invention, an error of a peak at a chemical shift (ppm) in a solid $^{13}$C-NMR chart is about ±1.0 ppm, and an error of a peak at an absorption band (cm-1) in an infrared absorption spectrum is about ±2 $cm^{-1}$.

The pharmaceutical composition of the present invention has characteristic peaks at at least 5 or more diffraction angles (2θ±0.2°) selected from 6.5, 7.8, 9.6, 12.4, 18.8, 21.2, 23.0, 24.5, and 26.0 (°) in powder X-ray diffraction, preferably has characteristic peaks at diffraction angles (2θ±0.2°) of 6.5, 7.8, 9.6, 12.4, 18.8, 21.2, 23.0, 24.5, and 26.0 (°).

The pharmaceutical composition of the present invention preferably has characteristic peaks at chemical shift values [δ (ppm)] of 162.6, 130.4, 103.1, 82.7, 73.3, 41.9, and 19.9 in a solid $^{13}$C-NMR chart.

The pharmaceutical composition of the present invention preferably has characteristic peaks at at least 5 or more absorption bands selected from 1663, 1352, 1225, 1156, 1032, 720, and 553 ($cm^{-1}$) in an infrared absorption spectrum, more preferably has characteristic peaks at absorption bands of 1663, 1352, 1225, 1156, 1032, 720, and 553 ($cm^{-1}$).

The pharmaceutical composition of the present invention can be produced by physical mixing. The physical mixing refers to a production method that does not include a step in which the compound 1 or a pharmaceutically acceptable salt thereof is converted into a solution state when the pharmaceutical composition is produced. As the physical mixing, mixing to form a uniform composition by applying an appropriate operation to two or more types of solids containing the compound 1 or a pharmaceutically acceptable salt thereof, a granulation that is performed when the compound 1 or a pharmaceutically acceptable salt thereof is in a solid state, and the like are exemplified.

Examples of a granulation method that can be used when the pharmaceutical composition of the present invention is produced include a dry granulation method and a wet granulation method. Specific examples of the dry granulation method include a crushing granulation method. Further, examples of the wet granulation method include a fluidized bed granulation method, a rolling bed granulation method, an extrusion granulation method, and a high shear granulation method, and preferred is a fluidized bed granulation method.

In the physical mixing, a solvent can be added as needed. As the type of the solvent, water, ethanol, a water-ethanol mixed solution, and the like are exemplified, and preferred is water. When such a solvent is used in the physical mixing, the pharmaceutical composition of the present invention may be used as it is or after it is dried.

In the physical mixing, a fluidizer or the like can be further added. Examples of the fluidizer include silicic acid derivatives such as light anhydrous silicic acid, calcium silicate, magnesium aluminometasilicate, talc, aluminum silicate, and hydrated silicon dioxide, and preferred is light anhydrous silicic acid.

In the physical mixing, a binder can be added. As the binder, a cellulose derivative, starch, povidone, or polyvinyl alcohol can be exemplified. Examples of the cellulose derivative include hydroxypropyl cellulose, hypromellose, and methylcellulose, and preferred is hydroxypropyl cellulose.

Here, the amount of the fluidizer to be used in the present invention is generally 10 mass % or less, preferably from 0.1 to 2 mass %, more preferably from 0.2 to 1 mass % with respect to the total pharmaceutical composition.

Examples of the pharmaceutical composition of the present invention include a tablet, a granule, a powder, and a fine granule, and preferred is a tablet or a granule. In the tablet, the granule, the powder, and the fine granule, a powdery granular material that is rapidly dissolved in the oral cavity and can be taken without water is included.

Further, as the pharmaceutical composition of the present invention, a tablet can be adopted. The tablet can also be produced using commonly known excipients, and it is also possible to prepare a tablet from the above-mentioned granule using commonly known methods. As the shape of the tablet, a generally used shape such as a cylindrical shape, a disk shape, a lenticular shape, or a rod-like shape can be adopted. The size of the tablet is not particularly limited as long as a human can orally take it, however, the maximum diameter (diameter) is preferably 15 mm or less, more preferably 10 mm or less. Further, in consideration of absorbability and administration to children, etc., the maximum diameter is further more preferably 5 mm or less. Further, in consideration of the absorbability and the ease of preparation of the pharmaceutical composition of the present invention, a tablet having a cylindrical shape with a maximum diameter of 4 mnm or less is preferred. The lower limit of the maximum diameter of the tablet is not particularly limited, but is generally 2 mm or more from the viewpoint of handling.

Further, when a tablet having a cylindrical shape with a diameter of 5 mm or less is adopted as the pharmaceutical composition of the present invention, the weight of the compound 1 per tablet is 10 mg or less from the viewpoint of the size and the absorbability of the tablet. After preparation of the tablet, an operation of packing a plurality of tablets in one package is sometimes generated. In that case, if there is a large difference in the diameter and the thickness of the cylindrical shape, it takes time when adjusting the packing amount by a counting plate with holes, and during the process, a few tablets may enter the hole of the counting plate or no tablet may enter the hole, and therefore, excess or shortage of the packing amount may occur. Therefore, in the case of the tablet having a cylindrical shape with a diameter of 5 mm or less, the ratio of the thickness to the diameter of the cylindrical shape is typically from 60 to 140% as an example, preferably from 80 to 120%.

Further, in the pharmaceutical composition of the present invention, other than the compound 1 or a pharmaceutically acceptable salt thereof and hydroxypropyl-β-cyclodextrin, other excipients may be blended as needed. The excipients are not particularly limited as long as it is generally used in drug products in the pharmaceutical field, and for example, a fluidizer, a diluent, a binder, a disintegrant, a lubricant, a coating agent, a colorant, a flavor, a taste masking agent, and the like can be exemplified, however, it is not limited thereto.

The pharmaceutical composition of the present invention is useful as an antitumor agent because the compound 1 has excellent c-Met inhibitory activity and VEGFR2 inhibitory activity. A target cancer is not particularly limited, however, examples thereof include head and neck cancer, gastrointestinal cancer [for example, esophageal cancer, gastric cancer, gastrointestinal stromal tumors, duodenal cancer, liver cancer, biliary tract cancer (for example, gallbladder and bile duct cancer, etc.), pancreatic cancer, small intestine cancer, large bowel cancer (for example, colorectal cancer, colon cancer, rectal cancer, etc.), etc.], lung cancer, breast cancer, ovarian cancer, uterine cancer (for example, cervical cancer, endometrial cancer, etc.), kidney cancer, bladder cancer, prostate cancer, urothelial cancer, bone and soft tissue sarcoma, blood cancer (for example, B cell lymphoma, chronic lymphocytic leukemia, peripheral T-cell lymphoma, myelodysplastic syndrome, acute myelogenous leukemia, acute lymphocytic leukemia, etc.), multiple myeloma, skin cancer, and mesothelioma.

EXAMPLES

Hereinafter, the present invention will be further specifically described with reference to Examples, however, the invention is not limited thereto. Although the invention is sufficiently described by Examples, it is to be understood that various changes and modifications can be made by a person skilled in the art. Therefore, such changes or modifications are included in the invention unless they depart from the scope of the invention.

As various types of reagents used in Examples, commercially available products were used unless otherwise indicated.

<Powder X-Ray Diffraction Spectrum (XRD) Measurement>

Powder X-ray diffraction was performed by lightly crushing an appropriate amount of a test specimen in an agate mortar according to need and then performing measurement according to the following test conditions.
  Apparatus: RINT-2100 Ultima/PC (manufactured by Rigaku Corporation)
  Target: CuKα.
  Scanning range: 5.0 to 40.0°
  Sampling width: 0.02°
  Scanning speed: 2°/min The handling of the apparatus including data processing was performed according to the method and procedure designated for each apparatus.

<Proton Nuclear Magnetic Resonance ($^{13}$C-NMR) Measurement>

$^{13}$C-NMR measurement was performed by CMX-300 Infinity (75.188829 MHz, manufactured by Chemagnetic, Inc.) using tetramethylsilane as an internal reference in the case where tetramethylsilane was contained in a deuterated solvent, and using an NMR solvent as an internal reference in the other cases. In each $^3$C-NMR chart obtained, all the d values were expressed in ppm.

<Infrared Absorption Spectrum (IR) Measurement>

IR measurement was performed using FT-730 (HORIBA, Ltd.) by the KBr method.

[Test Example 1] Solubility Test 1

Formulation Example 1

HP-β-CD (0.5925 g) was dissolved in a diluted McIlvaine buffer at pH 3.0 (50 mL), followed by heating to 37° C., whereby a test solution was obtained.

Comparative Example 1

A test solution was obtained by heating a diluted McIlvaine buffer at pH 3.0 (50 mL) to 37° C.

Comparative Example 2

A test solution was obtained in the same manner as in Formulation Example 1 using γ-CD (0.5925 g) in place of HP-β-CD (0.5925 g).

Comparative Example 3

A test solution was obtained in the same manner as in Formulation Example 1 using SBE-β-CD (0.5925 g) in place of HP-β-CD (0.5925 g).

With respect to Formulation Example 1, Comparative Example 1, and Comparative Example 2, the solubility of the compound 1 over time was measured. To each of the test solutions, a mesylate salt of the compound 1 (0.1185 g) was added, followed by stirring at 37° C. using a magnetic stirrer. The compositions of Formulation Example 1, Comparative Example 1, Comparative Example 2, and Comparative Example 3 are shown in Table 1.

TABLE 1

| (unit: parts by mass) | Formulation Example 1 | Comparative Example 1 | Comparative Example 2 | Comparative Example 3 |
|---|---|---|---|---|
| Mesylate salt of Compound 1 | 1.0 | 1.0 | 1.0 | 1.0 |
| HP-β-CD | 5.0 | — | — | — |
| γ-CD | — | — | 5.0 | — |
| SBE-β-CD | — | — | — | 5.0 |

The concentration of the compound 1 in the test solution was measured after 30, 60, 120, and 240 minutes from the start of the test using liquid chromatography (HPLC) under the following conditions.
  Apparatus: Alliance 2690 (manufactured by Waters, Inc.)
  Mobile phase A: 10 mM $Na_2HPO_4$ aqueous solution (pH 6.5)
  Mobile phase B: acetonitrile
  Gradient: mobile phase A/mobile phase B=6/4 (v/v)
  Column: L-column 2 ODS, 100 mm×3.0 mm, i.d.: 3 μm
  Measurement wavelength: 240 nm The handling of the apparatus including data processing was performed according to the method and procedure designated for each apparatus. The results are shown in Table 2.

TABLE 2

|  | After 30 min μg/mL | After 60 min μg/mL | After 120 min μg/mL | After 240 min μg/mL |
|---|---|---|---|---|
| Formulation Example 1 | 269.18 | 231.32 | 240.58 | 220.64 |
| Comparative Example 1 | 17.65 | 15.89 | 14.61 | 11.29 |
| Comparative Example 2 | 107.58 | 129.08 | 114.78 | 98.46 |

As shown in Table 2, it was found that when the same amount of a cyclodextrin derivative is present, HP-β-CD shows a higher solubility than γ-CD. On the other hand, in the case of SBE-β-CD, the error of the concentration of the compound 1 at each measurement time is large, and it is difficult to predict the absorbability thereof when it is administered to a human, and therefore, it was found that SBE-β-CD is not suitable for formulation with the compound 1.

[Test Example 2] Solubility Test 2

Formulation Example 2

A test solution was obtained in the same manner as in Formulation Example 1 using HP-β-CD (0.0593 g) in place of HP-β-CD (0.5925 g).

Formulation Example 3

A test solution was obtained in the same manner as in Formulation Example 1 using HP-β-CD (0.1185 g) in place of HP-β-CD (0.5925 g).

Formulation Example 4

A test solution was obtained in the same manner as in Formulation Example 1 using HP-β-CD (0.3555 g) in place of HP-β-CD (0.5925 g).

With respect to Formulation Examples 1 to 4, the solubility of the compound 1 over time was measured in the same manner as in the Test Example 1. To each of the test solutions, a mesylate salt of the compound 1 (0.1185 g) was added, followed by stirring at 37° C. using a magnetic stirrer. The compositions of Formulation Examples 1 to 4 are shown 2 in Table 3.

TABLE 3

| (unit: parts by mass) | Formulation Example 1 | Formulation Example 2 | Formulation Example 3 | Formulation Example 4 |
|---|---|---|---|---|
| Mesylate salt of Compound 1 | 1.0 | 1.0 | 1.0 | 1.0 |
| HP-β-CD | 5.0 | 0.5 | 1.0 | 3.0 |

The concentration of the compound 1 in the test solution was measured after 30, 60, 120, and 240 minutes from the start of the test using liquid chromatography (HPLC) under the same conditions. The results are shown in Table 4.

TABLE 4

|  | After 30 min µg/mL | After 60 min µg/mL | After 120 min µg/mL | After 240 min µg/mL |
|---|---|---|---|---|
| Formulation Example 1 | 269.18 | 231.32 | 240.58 | 220.64 |
| Formulation Example 2 | 39.04 | 30.94 | 35.96 | 30.24 |
| Formulation Example 3 | 59.56 | 61.58 | 54.60 | 50.36 |
| Formulation Example 4 | 137.36 | 139.50 | 157.22 | 140.02 |

As shown in Table 4, it was found that the solubility of the mesylate salt of the compound 1 is improved in the presence of HP-β-CD, and it shows a higher solubility as HP-β-CD is present in a larger amount.

[Test Example 3] XRD Measurement

Formulation Example 5

A physically mixed product (26.6 g, PM product) of a mesylate salt of the compound 1 was obtained by mixing the mesylate salt of the compound 1 (5.0 g) and HP-β-CD (22.8 g) in a mortar.

Figure 2:
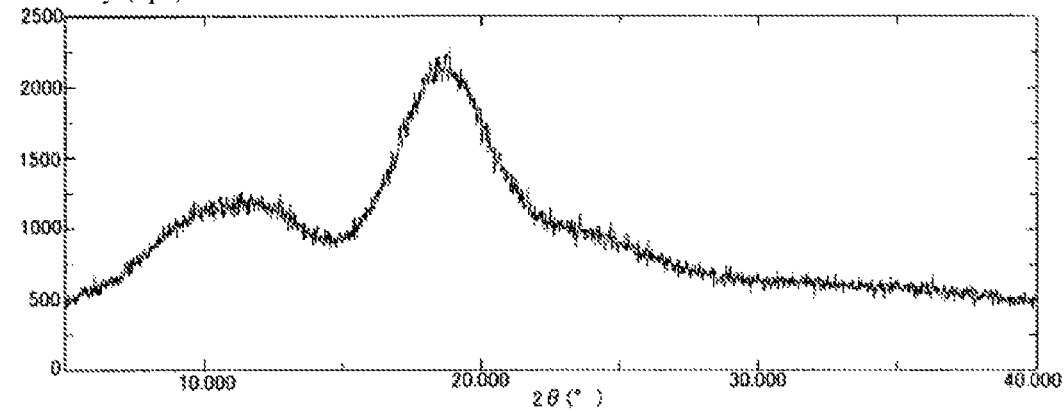
FIG. 2 shows the results of XRD measurement of HP-β-CD.
Figure 3:
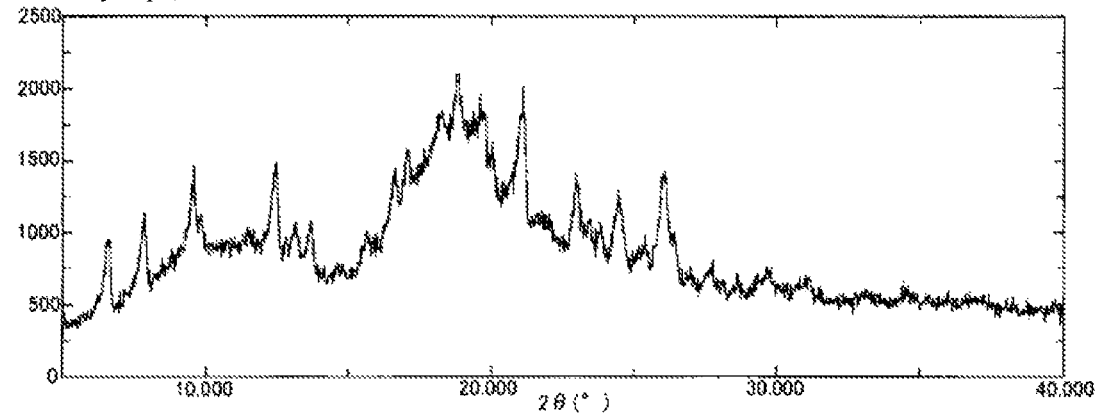
FIG. 3 shows the results of XRD measurement of a physically mixed product of a mesylate salt of the compound 1 and HP-β-CD.
Figure 4:
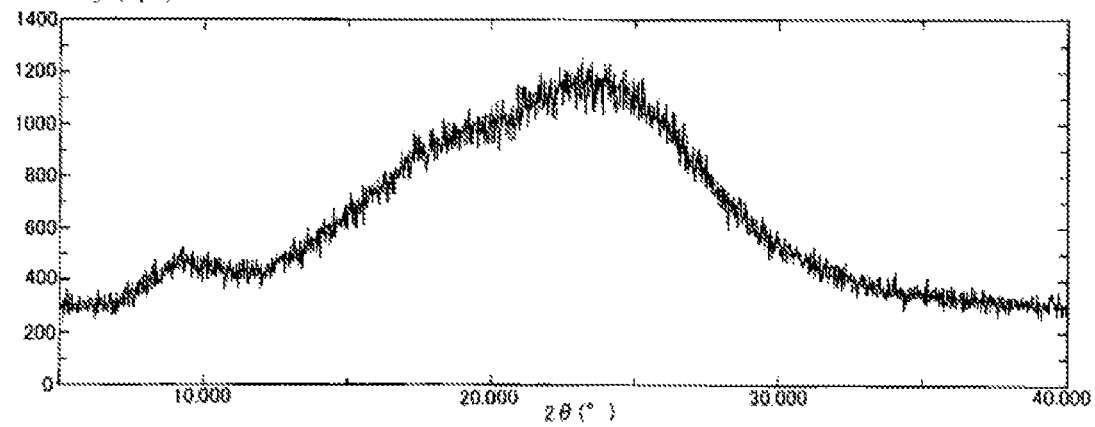
FIG. 4 shows the results of XRD measurement of a spray-dried product of a mesylate salt of the compound 1 and HP-β-CD.

The results of powder X-ray diffraction spectrum (XRD) measurement of the mesylate salt of the compound 1 are shown in FIG. 1, the results of XRD measurement of HP-β-CD are shown in FIG. 2, the results of XRD measurement of the physically mixed product of the mesylate salt of the compound 1 and HP-β-CD obtained in Formulation Example 5 are shown in FIG. 3, and the XRD measurement of a spray-dried product of the mesylate salt of the compound 1 and HP-β-CD obtained in Comparative Example 4 described below are shown in FIG. 4.

Based on these, it was found that in the XRD measurement of the physically mixed product of the mesylate salt of the compound 1 and HP-β-CD, the product has characteristic peaks at diffraction angles (2θ±0.2°) of 6.5, 7.8, 9.6, 12.4, 18.8, 21.2, 23.0, 24.5, and 26.0 (°) derived from the mesylate salt of the compound 1.

[Test Example 4] $^{13}$C-NMR Measurement

Figure 5:
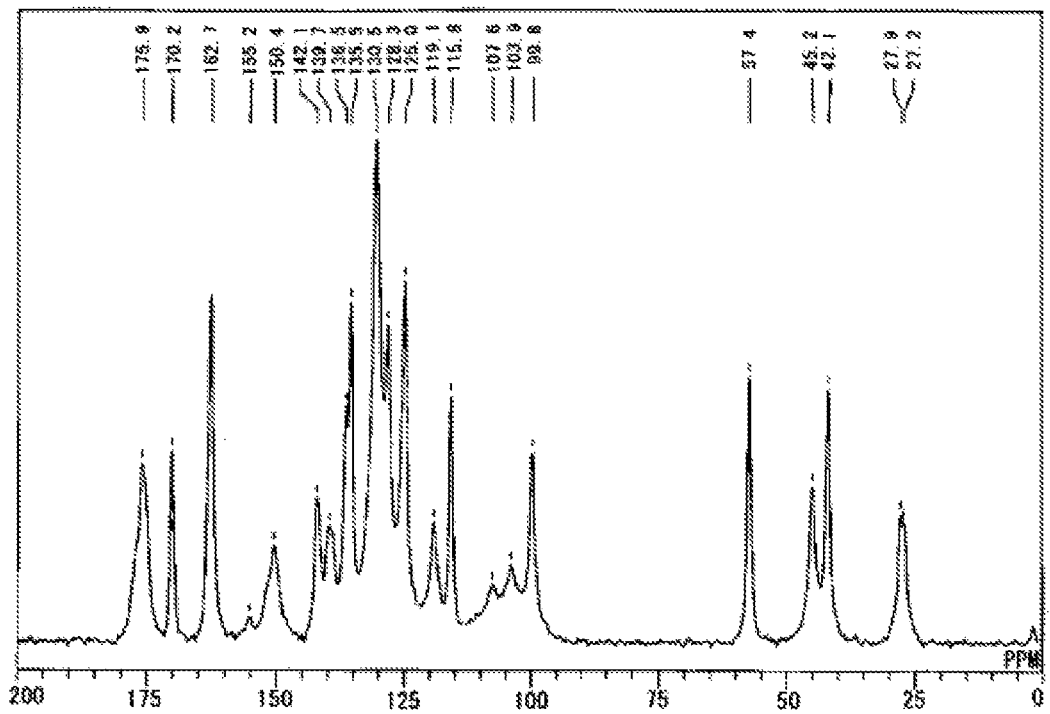
FIG. 5 shows the results of solid proton nuclear magnetic resonance ($^{13}$C-NMR) measurement of a mesylate salt of the compound 1.
Figure 6:
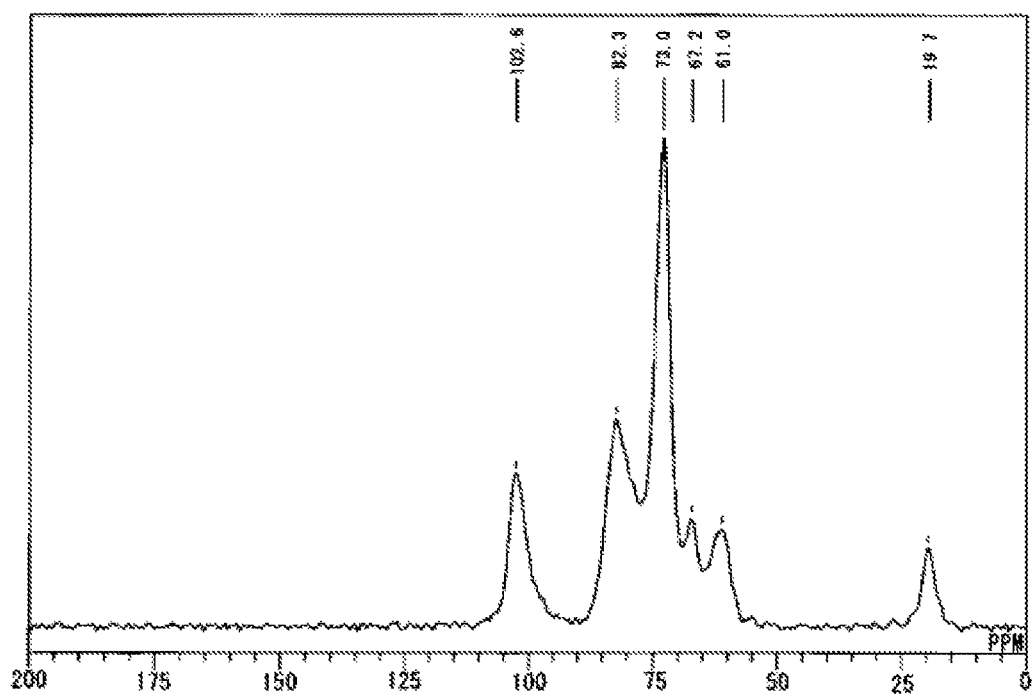
FIG. 6 shows the results of $^{13}$C-NMR measurement of HP-β-CD.
Figure 7:
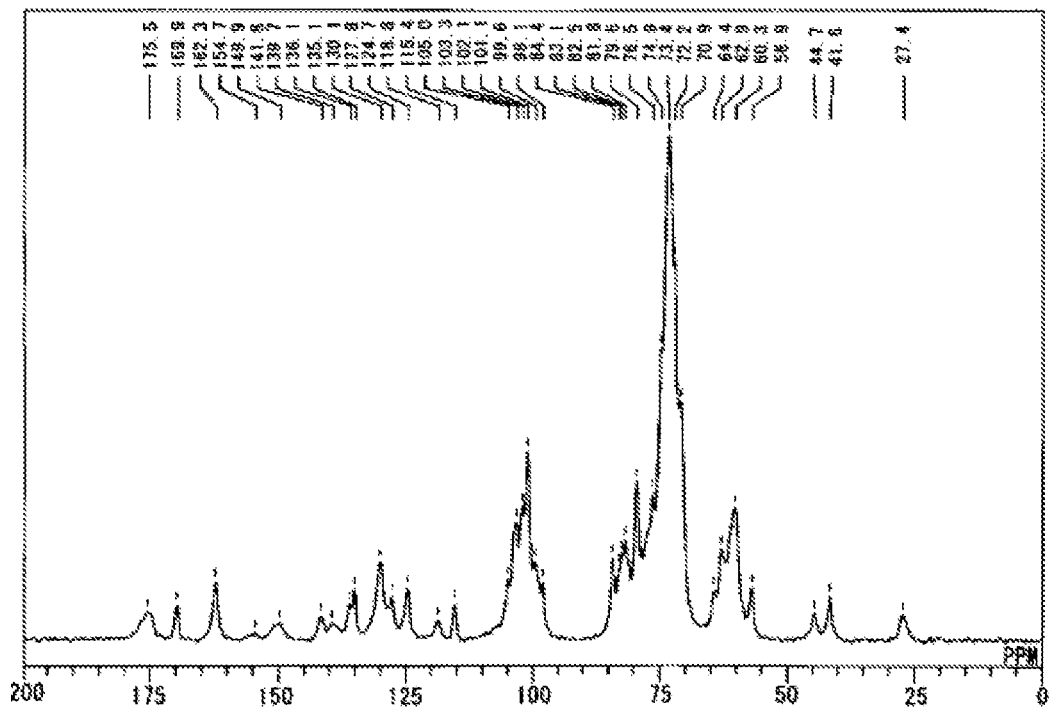
FIG. 7 shows the results of $^{13}$C-NMR measurement of a physically mixed product of a mesylate salt of the compound 1 and HP-β-CD.

The results of solid proton nuclear magnetic resonance ($^{13}$C-NMR) measurement of the mesylate salt of the compound 1 are shown in FIG. 5, the results of $^{13}$C-NMR measurement of HP-β-CD are shown in FIG. 6, and the results of $^{13}$C-NMR measurement of the physically mixed product of the mesylate salt of the compound 1 and HP-β-CD obtained in Formulation Example 5 are shown in FIG. 7.

Based on these, it was found that in the solid proton nuclear magnetic resonance ($^{13}$C-NMR) measurement of the physically mixed product of the mesylate salt of the compound 1 and HP-β-CD, the product has characteristic peaks at chemical shift values [δ (ppm)] of 162.6, 130.4, 103.1, 82.7, 73.3, 41.9, and 19.9 derived from the mesylate salt of the compound 1.

[Test Example 5] IR Measurement

Figure 8:
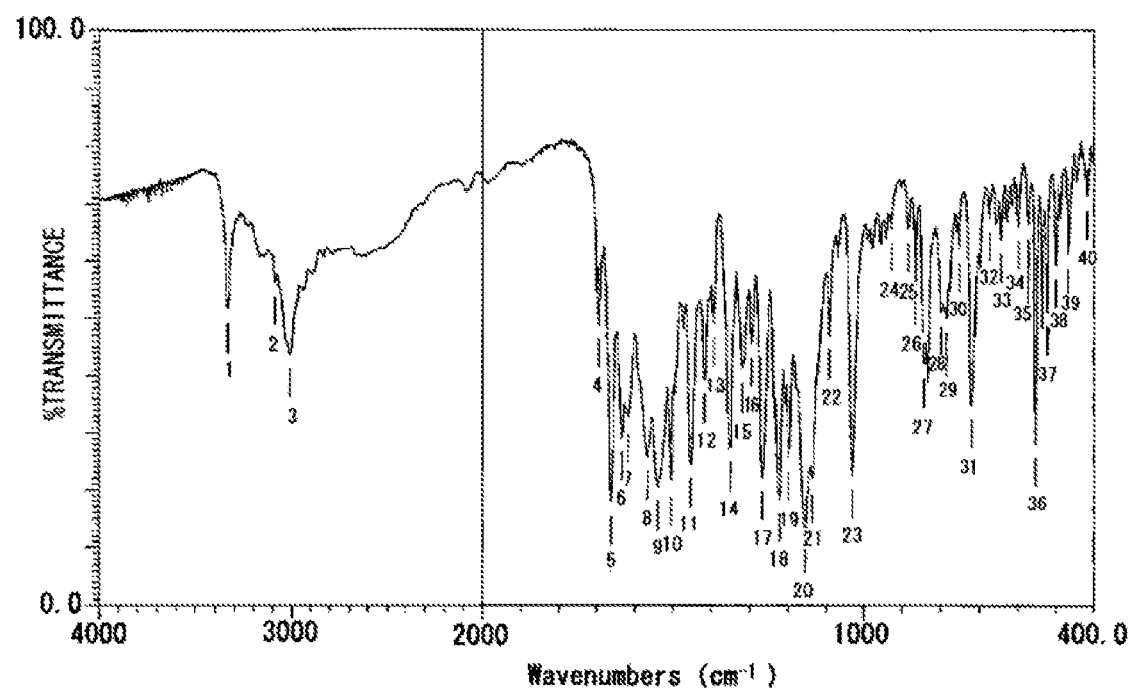
FIG. 8 shows the results of infrared absorption spectrum (IR) measurement of a mesylate salt of the compound 1.
Figure 9:
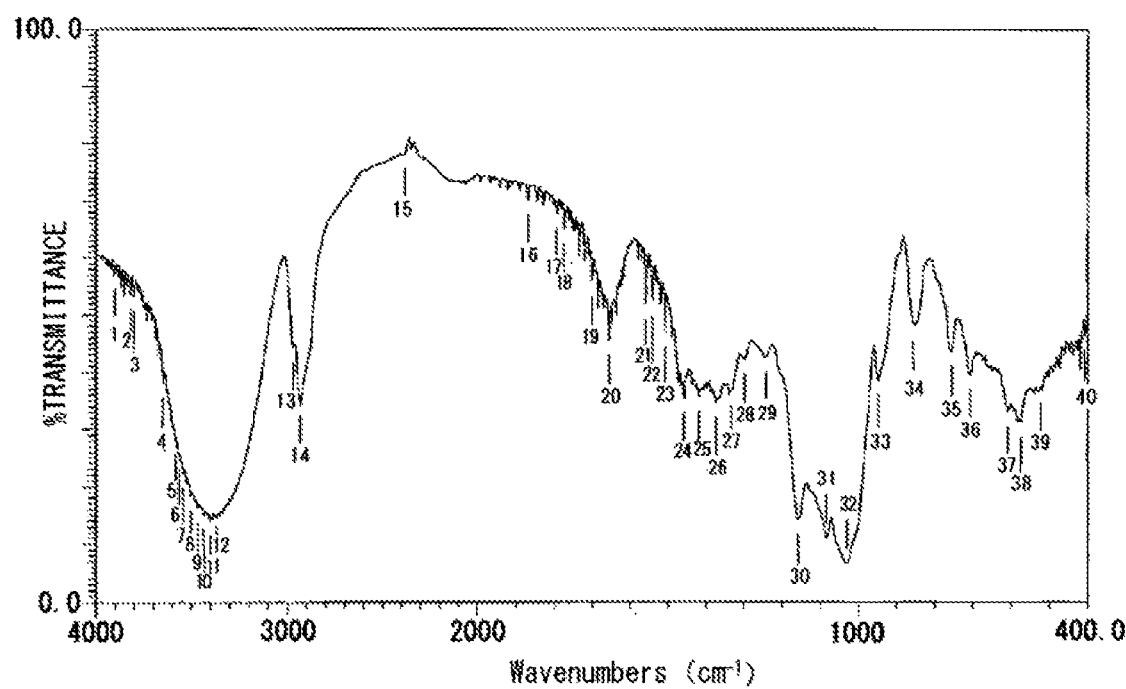
FIG. 9 shows the results of IR measurement of HP-β-CD.
Figure 10:
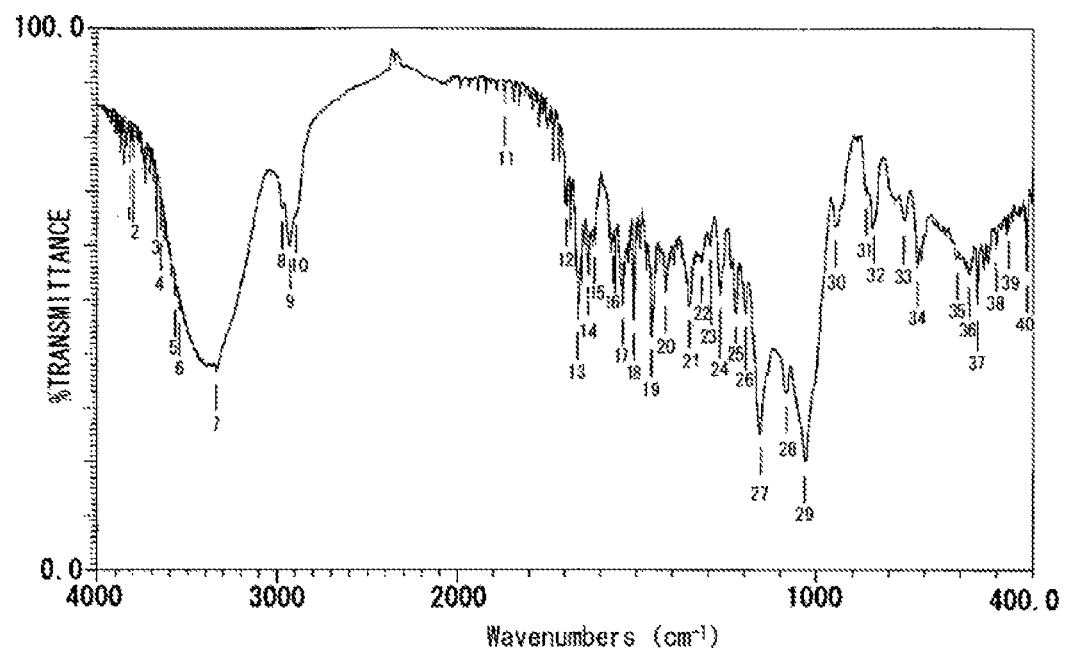
FIG. 10 shows the results of IR measurement of a physically mixed product of a mesylate salt of the compound 1 and HP-β-CD.
Figure 11:
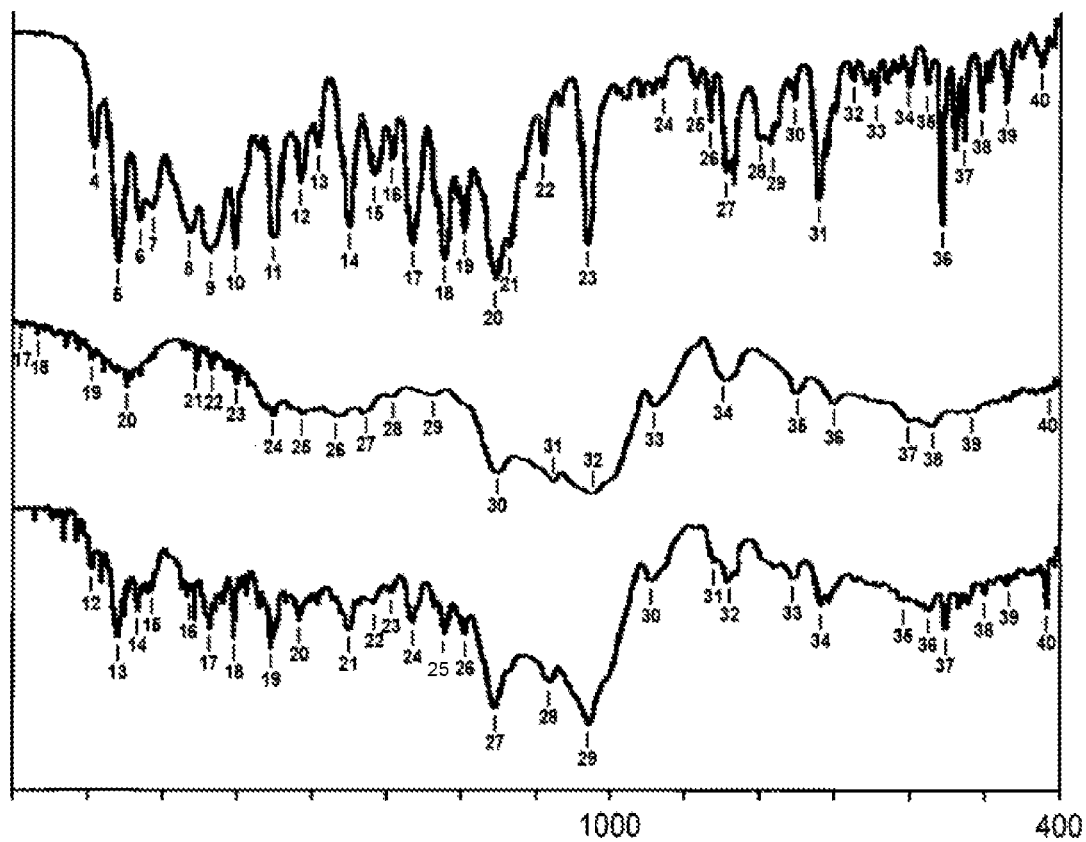
FIG. 11 shows the results of IR measurement in the fingerprint regions of a mesylate salt of the compound 1, HP-β-CD, and a physically mixed product of the mesylate salt of the compound 1 and HP-β-CD in this order from the top.

The results of infrared absorption spectrum (IR) measurement of the mesylate salt of the compound 1 are shown in FIG. 8, the results of IR measurement of HP-β-CD are shown in FIG. 9, and the results of IR measurement of the physically mixed product of the mesylate salt of the compound 1 and HP-β-CD obtained in Formulation Example 5 are shown in FIG. 10. Further, IR measurement in the fingerprint regions thereof is shown in FIG. 11.

Based on these, it was found that in the infrared absorption spectrum measurement of the physically mixed product of the mesylate salt of the compound 1 and HP-β-CD, the product has characteristic peaks at absorption bands (cm$^{-1}$) of 1663, 1352, 1225, 1156, 1032, 720, and 553 derived from the mesylate salt of the compound 1.

[Test Example 6] Stability Test

Comparative Example 4

A mesylate salt of the compound 1 (5.0 g) and HP-β-CD (22.8 g) were dissolved in a mixed solution of water (100.0 g), ethanol (250.0 g) and dichloromethane (150.0 g), followed by spray drying by a spray dryer (GB22, manufactured by Yamato Scientific Co., Ltd.), whereby a spray-dried product (19.2 g, SD product) of the mesylate salt of the compound 1 was obtained.

The compositions and the preparation methods of Formulation Example 5 and Comparative Example 4 are shown in Table 5.

TABLE 5

| (unit: parts by mass) | Formulation Example 5 | Comparative Example 4 |
|---|---|---|
| Mesylate salt of Compound 1 | 1.0 | 1.0 |
| HP-β-CD | 4.6 | 4.6 |
| Preparation method | PM product | SD product |

With respect to Formulation Example 5 and Comparative Example 4, a change in the total amount of the related substances of the compound 1 in each formulation over time was evaluated. Each formulation was wrapped with a polyethylene/cellophane laminated film and then enclosed in an aluminum bag with a desiccant and an deoxygenating agent, and the concentration of the compound 1 in the formulations stored at 5, 25, and 40° C. for 1 month and the formulations stored at 60° C. for 1 week was measured using liquid chromatography (HPLC) under the following conditions.
  Apparatus: Alliance 2690 (manufactured by Waters, Inc.)
  Mobile phase A: 10 mM $Na_2HPO_4$ aqueous solution (pH 6.5)
  Mobile phase B: acetonitrile
  Gradient: shown in Table 6
  Column: L-column 2 ODS, 150 mm×4.6 mm, i.d.: 5 µm
  Measurement wavelength: 220 nm

TABLE 6

| Time (min) | Mobile phase A (%) | Mobile phase B (%) |
|---|---|---|
| 0 | 64 | 36 |
| 1 | 64 | 36 |
| 11 | 55 | 45 |
| 16 | 52 | 48 |
| 20 | 37 | 63 |
| 30 | 37 | 63 |
| 31 | 64 | 36 |
| 40 | 64 | 36 |

The handling of the apparatus including data processing was performed according to the method and procedure designated for each apparatus. The results are shown in Table 7.

TABLE 7

|  | 0 value | 5° C. 1 month | 25° C. 1 month | 40° C. 1 month | 60° C. 1 week |
|---|---|---|---|---|---|
| Formulation Example 5 | 0.25 | 0.37 | 0.39 | 0.38 | 0.30 |
| Comparative Example 4 | 1.27 | 1.45 | 2.10 | 3.15 | 3.18 |

As shown in Table 7, it was found that the physically mixed product of the mesylate salt of the compound 1 and HP-β-CD has excellent stability as compared with the spray-dried product.

[Test Example 7] Absorbability Test 1

Comparative Example 5

Granulation was performed using a high shear granulator (FM-VG-25, manufactured by Powrex Corporation) while adding a 14% povidone solution (466 g) to a mesylate salt of the compound 1 (1564.2 g), D-mannitol (1188 g), and sodium starch glycolate (33 g), whereby a wet powder was obtained. The wet powder was dried using a fluidized bed granulator (NFLO-5, manufactured by Freund Corporation), and then mixed using a mixer (CV-20, manufactured by Tokuju Corporation) with sodium starch glycolate (158.4 g) and magnesium stearate (26.4 g), whereby granules for tableting were obtained. The granules for tableting were compressed into tablets using a tableting machine (VELG 0512SW2MZ, manufactured by Kikusui Seisakusho Ltd.), and thereafter, a coating solution obtained by adding hypromellose (64.8 g), macrogol 6000 (8.1 g), titanium oxide (8.1 g), and yellow ferric oxide (0.081 g) was sprayed thereon using a coating machine (DRC-300, manufactured by Powrex Corporation), whereby coated tablets were obtained.

The compositions and the preparation methods of Formulation Example 5, Comparative Example 4, and Comparative Example 5 are shown in Table 8.

TABLE 8

| (unit: parts by mass) | Formulation Example 5 | Comparative Example 4 | Comparative Example 5 |
|---|---|---|---|
| Mesylate salt of Compound 1 | 1.0 | 1.0 | 1.0 |
| HP-β-CD | 4.6 | 4.6 | — |
| D-mannitol | — | — | 0.76 |
| Sodium starch glycolate | — | — | 0.12 |
| Povidone | — | — | 0.04 |
| Magnesium stearate | — | — | 0.02 |
| Hypromellose | — | — | 0.04 |
| Preparation method | PM product | SD product | PM product |

With respect to Formulation Example 5, Comparative Example 4, and Comparative Example 5, each formulation was administered to animals under the following conditions, and the absorbability was evaluated.
  Animals used: beagle dogs (3 male animals, Kitayama Labes Co., Ltd.)
  Feeding Conditions: fasting for 20 hours from the previous day
  Dose: 100 mg/body (in terms of the compound 1)
  Administration method: administered with 50 mL water
  Pretreatment: Pentagastrin was intramuscularly administered (10 µg/0.1 mL/kg) 30 minutes before administering the formulation and thereafter administered twice at an interval of 45 minutes. An atropine sulfate intravenous injection was intravenously administered (20 µg/0.04 mL/kg) 30 minutes before administering the formulation.
The results are shown in Table 9.

TABLE 9

|  | AUC ng · hr/mL |
|---|---|
| Formulation Example 5 | 6842 |
| Comparative Example 4 | 5789 |
| Comparative Example 5 | 1666 |

As shown in Table 9, it was found that the absorption of the mesylate salt of the compound 1 is improved by the addition of HP-β-CD, and the physically mixed product of the mesylate salt of the compound 1 and HP-β-CD shows absorbability comparable to the spray-dried product.

[Test Example 8] Absorbability Test 2

Formulation Example 6

Granulation was performed using a fluidized bed granulator (FL-LABO (special), manufactured by Freund Corporation) while spraying a 5% hydroxypropyl cellulose solution (1000 g) onto a mesylate salt of the compound 1 (296.3 g), HP-β-CD (1350 g), and light anhydrous silicic acid (8.8 g), whereby a granulated material was obtained. Magnesium 2 stearate (10 g) was added to the granulated material and mixed in a polyethylene bag, whereby granules were obtained.

The compositions of Formulation Example 5 and Formulation Example 6 are shown in Table 10.

TABLE 10

| (unit: parts by mass) | Formulation Example 5 | Formulation Example 6 |
| --- | --- | --- |
| Mesylate salt of Compound 1 | 1.0 | 1.0 |
| HP-β-CD | 4.6 | 4.6 |
| Light anhydrous silicic acid | — | 0.03 |
| Hydroxypropyl cellulose | — | 0.17 |
| Magnesium stearate | — | 0.03 |

With respect to Formulation Example 5 and Formulation Example 6, each formulation was administered to animals under the following conditions, and the absorbability was evaluated.
Animals used: beagle dogs (3 male animals, Kitayama Labes Co., Ltd.)
Feeding Conditions: fasting for 20 hours from the previous day
Dose: 400 mg/body (in terms of the compound 1)
Administration method: administered with 50 mL water
Pretreatment: Pentagastrin was intramuscularly administered (10 μg/0.1 mL/kg) 30 minutes before administering the formulation and thereafter administered twice at an interval of 45 minutes. An atropine sulfate intravenous injection was intravenously administered (20 μg/0.04 mL/kg) 30 minutes before administering the formulation.
The results are shown in Table 11.

TABLE 11

| | AUC ng · hr/mL |
| --- | --- |
| Formulation Example 5 | 11258 |
| Formulation Example 6 | 12810 |

As shown in Table 11, it was found that the granules obtained by granulating the mesylate salt of the compound 1 and HP-β-CD show absorbability comparable to the physically mixed product thereof.

[Test Example 9] Absorbability Test 3

Formulation Example 7

Granulation was performed using a fluidized bed granulator (NFLO-5, manufactured by Freund Corporation) while spraying a 5% hydroxypropyl cellulose solution (3000 g) onto a mesylate salt of the compound 1 (888.8 g), HP-β-CD (4050 g), and light anhydrous silicic acid (26.3 g), whereby a granulated material was obtained. Two batches of the granulated material were mixed using a mixer (CV-20, manufactured by Tokuju Corporation) with magnesium stearate (60 g), whereby granules were obtained.

Formulation Example 8

Granulation was performed using a fluidized bed granulator (NFLO-5, manufactured by Freund Corporation) while spraying a 5% hydroxypropyl cellulose solution (3000 g) onto a mesylate salt of the compound 1 (888.8 g), HP-β-CD (4050 g), and light anhydrous silicic acid (26.3 g), whereby a granulated material was obtained. Magnesium stearate (2.16 g) was added to a portion (396.4 g) of the granulated material and mixed in a polyethylene bag, whereby granules were obtained. The granules were compressed into tablets with a diameter of 4 mm using a tableting machine (VELG 0512SW2MZ, manufactured by Kikusui Seisakusho Ltd.), and thereafter, a coating solution obtained by adding water (480.0 g), hypromellose (32.0 g), macrogol 6000 (4.0 g), titanium oxide (4.0 g), and yellow ferric oxide (0.2 g) was sprayed thereon using a coating machine (HC-FZ-LABO, manufactured by Freund Corporation), whereby coated tablets of the tablets with a diameter of 4 mm were obtained.

Formulation Example 9

A portion (292.1 g) of the granules obtained in Formulation Example 7 were compressed into tablets with a diameter of 3.5 mm using a tableting machine (VELG 0512SW2MZ, manufactured by Kikusui Seisakusho Ltd.), and thereafter, a coating solution obtained by adding water (540.0 g), hypromellose (48.0 g), macrogol 6000 (6.0 g), titanium oxide (6.0 g), and yellow ferric oxide (0.3 g) was sprayed thereon using a coating machine (HC-FZ-LABO, manufactured by Freund Corporation), whereby coated tablets of the tablets with a diameter of 3.5 mm were obtained.

The compositions and dosage forms of Formulation Examples 7 to 9 are shown in Table 12.

TABLE 12

| (unit: parts by mass) | Formulation Example 7 | Formulation Example 8 | Formulation Example 9 |
| --- | --- | --- | --- |
| Mesylate salt of Compound 1 | 1.0 | 1.0 | 1.0 |
| HP-β-CD | 4.6 | 4.6 | 4.6 |
| Light anhydrous silicic acid | 0.030 | 0.030 | 0.030 |
| Hydroxypropyl cellulose | 0.17 | 0.17 | 0.17 |
| Magnesium stearate | 0.034 | 0.031 | 0.031 |
| Hypromellose | — | 0.14 | 0.14 |
| Macrogol 6000 | — | 0.017 | 0.017 |
| Titanium oxide | — | 0.017 | 0.017 |
| Yellow ferric oxide | — | 0.00084 | 0.00084 |
| Dosage form | Granule | Tablet with diameter of 4 mm | Tablet with diameter of 3.5 mm |

With respect to these, each formulation was administered to animals under the following conditions, and the absorbability was evaluated.
Animals used: beagle dogs (6 male animals, Kitayama Labes Co., Ltd.)
Feeding Conditions: fasting for 20 hours from the previous day
Dose: 200 mg/body (in terms of the compound 1)
Administration method: administered with 50 mL water
Pretreatment: An atropine sulfate intravenous injection was intravenously administered (20 μg/0.04 mL/kg) 30 minutes before administering the formulation. When the test was performed at a low intragastric pH, pentagastrin was intramuscularly administered (10 μg/0.1 mL/kg) 30 minutes before administering the formulation and thereafter administered twice at an interval of 45 minutes, and when the test was performed at a high intragastric pH, omeprazole was intravenously administered (1 mg/0.25 mL/kg) 30 minutes before administering the formulation and 60 minutes thereafter once.

As a result, it was found that the tablets containing the mesylate salt of the compound 1 and HP-β-CD show absorbability comparable to the granules thereof without being affected by the intragastric pH.

While the present invention has been described in detail with reference to specific embodiments, it will be apparent to a person skilled in the art that various changes and modifications can be made without departing from the spirit and scope of the invention. This application is based on Japanese Patent Application filed on Feb. 15, 2017 (Patent Application No. 2017-026203), the entire contents of which are incorporated herein by reference. Further, all references cited herein are incorporated by reference in their entirety.

The invention claimed is:

1. A solid pharmaceutical composition, comprising:
   a mixture of 4-(2-fluoro-4-(3-(2-phenylacetyl)thioureido)phenoxy)-7-methoxy-N-methylquinoline-6-carboxamide or a pharmaceutically acceptable salt thereof; and
   hydroxypropyl-β-cyclodextrin;
   wherein the composition includes peaks at chemical shift values [δ (ppm)] of 162.6, 130.4, 103.1, 82.7, 73.3, 41.9, and 19.9 in solid 13C-NMR.

2. The pharmaceutical composition according to claim 1, wherein hydroxypropyl-β-cyclodextrin is contained at 0.1 to 5.5 parts by mass with respect to 1 part by mass of 4-(2-fluoro-4-(3-(2-phenylacetyl)thioureido)phenoxy)-7-methoxy-N-methylquinoline-6-carboxamide or a pharmaceutically acceptable salt thereof.

3. The pharmaceutical composition according to claim 1, wherein hydroxypropyl-β-cyclodextrin is contained at 4.0 to 5.0 parts by mass with respect to 1 part by mass of 4-(2-fluoro-4-(3-(2-phenylacetyl)thioureido)phenoxy)-7-methoxy-N-methylquinoline-6-carboxamide or a pharmaceutically acceptable salt thereof.

4. The pharmaceutical composition according to claim 1, further comprising:
   a fluidizer selected from light anhydrous silicic acid, calcium silicate, magnesium aluminometasilicate, talc, aluminum silicate, and hydrated silicon dioxide.

5. The pharmaceutical composition according to claim 4, wherein the fluidizer comprises from about 0.1 to 2 mass % of the total mass of the pharmaceutical composition.

6. The pharmaceutical composition according to claim 1, wherein the amount of hydroxypropyl-β-cyclodextrin is from about 76 to 85 mass % of the pharmaceutical composition.

7. The pharmaceutical composition according to claim 1, wherein the pharmaceutically acceptable salt is the mesylate and the composition includes peaks at 5 or more diffraction angles 2θ (±0.2°) selected from the group consisting of 6.5, 7.8, 9.6, 12.4, 18.8, 21.2, 23.0, 24.5, and 26.0 (°) in powder X-ray structure diffraction.

8. The pharmaceutical composition according to claim 1, wherein the pharmaceutically acceptable salt is the mesylate and the composition includes peaks at 5 or more diffraction angles 2θ (±0.2°) selected from the group consisting of 6.5, 7.8, 9.6, 12.4, 18.8, 21.2, 23.0, 24.5, and 26.0 (°) in powder X-ray structure diffraction.

9. The pharmaceutical composition according to claim 1, wherein the pharmaceutically acceptable salt is the mesylate and the composition includes peaks at 5 or more absorption bands selected from the group consisting of 1663, 1352, 1225, 1156, 1032, 720, and 553 (cm$^{-1}$) in an infrared absorption spectrum.

10. A solid pharmaceutical composition, comprising:
    4-(2-fluoro-4-(3-(2-phenylacetyl)thioureido)phenoxy)-7-methoxy-N-methylquinoline-6-carboxamide or a pharmaceutically acceptable salt thereof; and
    hydroxypropyl-β-cyclodextrin;
    wherein the composition includes peaks at 5 or more absorption bands selected from the group consisting of 1663, 1352, 1225, 1156, 1032, 720, and 553 (cm$^{1}$) in an infrared absorption spectrum.

11. The pharmaceutical composition according to claim 10, wherein hydroxypropyl-β-cyclodextrin is contained at 0.1 to 5.5 parts by mass with respect to 1 part by mass of 4-(2-fluoro-4-(3-(2-phenylacetyl)thioureido)phenoxy)-7-methoxy-N-methylquinoline-6-carboxamide or a pharmaceutically acceptable salt thereof.

12. The pharmaceutical composition according to claim 10, wherein hydroxypropyl-β-cyclodextrin is contained at 4.0 to 5.0 parts by mass with respect to 1 part by mass of 4-(2-fluoro-4-(3-(2-phenylacetyl)thioureido)phenoxy)-7-methoxy-N-methylquinoline-6-carboxamide or a pharmaceutically acceptable salt thereof.

13. The pharmaceutical composition according to claim 10, further comprising:
    a fluidizer selected from light anhydrous silicic acid, calcium silicate, magnesium aluminometasilicate, talc, and hydrated silicon dioxide.

14. The pharmaceutical composition according to claim 13, wherein the fluidizer comprises from about 0.1 to 2 mass % of the total mass of the pharmaceutical composition.

15. The pharmaceutical composition according to claim 10, wherein the amount of hydroxypropyl-Q-cyclodextrin is from about 76 to 85 mass % of the pharmaceutical composition.

16. The pharmaceutical composition according to claim 10, wherein the pharmaceutically acceptable salt is the mesylate and the composition includes peaks at 5 or more diffraction angles 2θ (±0.2°) selected from the group consisting of 6.5, 7.8, 9.6, 12.4, 18.8, 21.2, 23.0, 24.5, and 26.0 (°) in powder X-ray structure diffraction.

17. The pharmaceutical composition according to claim 10, wherein the pharmaceutically acceptable salt is the mesylate and the composition includes peaks at 5 or more diffraction angles 2θ (±0.2°) selected from the group consisting of 6.5, 7.8, 9.6, 12.4, 18.8, 21.2, 23.0, 24.5, and 26.0 (°) in powder X-ray structure diffraction.

18. The pharmaceutical composition according to claim 10, wherein the pharmaceutically acceptable salt is the mesylate and the composition includes peaks at chemical shift values [δ (ppm)] of 162.6, 130.4, 103.1, 82.7, 73.3, 41.9, and 19.9 in solid 13C-NMR.

19. A pharmaceutical composition, comprising:
    4-(2-fluoro-4-(3-(2-phenylacetyl)thioureido)phenoxy)-7-methoxy-N-methylquinoline-6-carboxamide or a pharmaceutically acceptable salt thereof; and
    hydroxypropyl-β-cyclodextrin;
    wherein the pharmaceutical composition is produced by physical mixing.

20. The pharmaceutical composition according to claim 19,
wherein the physical mixing is mixing, or a granulation.

21. The pharmaceutical composition according to claim 19,
wherein the physical mixing is mixing, a dry granulation method, or a wet granulation method.

22. The pharmaceutical composition according to claim 19,
wherein the physical mixing is a fluidized bed granulation method.

23. The pharmaceutical composition according to claim 19,
wherein the physical mixing does not include a step in which 4-(2-fluoro-4-(3-(2-phenylacetyl)thioureido)phenoxy)-7-methoxy-N-methylquinoline-6-carboxamide or a pharmaceutically acceptable salt thereof is converted into a solution state when the pharmaceutical composition is produced.

24. The pharmaceutical composition according to claim 19,
wherein the pharmaceutical composition includes peaks at chemical shift values [δ (ppm)] of 162.6, 130.4, 103.1, 82.7, 73.3, 41.9, and 19.9 in solid 13C-NMR.

25. The pharmaceutical composition according to claim 19,
wherein the pharmaceutical composition includes peaks at 5 or more absorption bands selected from the group consisting of 1663, 1352, 1225, 1156, 1032, 720, and 553 ($cm^{-1}$) in an infrared absorption spectrum.

\* \* \* \* \*